(12) United States Patent
Aranguren Caro et al.

(10) Patent No.: US 11,225,692 B2
(45) Date of Patent: Jan. 18, 2022

(54) SHRIMP DISEASE DETECTION ASSAYS AND USES THEREOF

(71) Applicant: Arizona Board of Regents on Behalf of the University of Arizona, Tucson, AZ (US)

(72) Inventors: Luis F. Aranguren Caro, Tucson, AZ (US); Arun Dhar, Tucson, AZ (US); Roberto Cruz Flores, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 255 days.

(21) Appl. No.: 16/542,510

(22) Filed: Aug. 16, 2019

(65) Prior Publication Data

US 2020/0056227 A1 Feb. 20, 2020

Related U.S. Application Data

(60) Provisional application No. 62/764,859, filed on Aug. 16, 2018.

(51) Int. Cl.
*C12Q 1/68* (2018.01)
*C07H 21/04* (2006.01)
*C12Q 1/689* (2018.01)

(52) U.S. Cl.
CPC ....... *C12Q 1/689* (2013.01); *C12Q 2600/158* (2013.01); *C12Q 2600/16* (2013.01)

(58) Field of Classification Search
None
See application file for complete search history.

(56) References Cited

PUBLICATIONS

Gen Bank Accession JQAJ01000001.1 , Aug. 2014.*

* cited by examiner

*Primary Examiner* — Jeanine A Goldberg
(74) *Attorney, Agent, or Firm* — Thomas|Horstemeyer LLP

(57) ABSTRACT

Described herein various PCR based assays that can detect *H. penaei* and/or *V. parahaemolyticus* that causes AHPND in a nucleic acid sample obtained from one or more shrimp. In some aspects, the PCR based assays can detect one or more of the following genes: the flgE gene from *H. penaei*, the shrimp 18s rRNA gene, the shrimp beta actin gene from shrimp, a bacterial 16S rRNA gene from bacteria (any type of bacteria) the *Vibrio* pirA gene, and the *Vibrio* pirB gene. The assays described herein can be single assays or can be multiplexed such that more than one gene and/or more than one bacterial species can be detected in a single reaction. Other compositions, compounds, methods, features, and advantages of the present disclosure will be or become apparent to one having ordinary skill in the art upon examination of the following drawings, detailed description, and examples.

19 Claims, 13 Drawing Sheets

Specification includes a Sequence Listing.

SHRIMP DISEASE DETECTION ASSAYS AND USES THEREOF

CROSS-REFERENCE TO RELATED APPLICATIONS

This application claims benefit of U.S. Provisional Application No. 62/764,859, filed Aug. 16, 2018, which is hereby incorporated herein by reference in its entirety.

SEQUENCE LISTING

This application contains a sequence listing filed in electronic form as an ASCII.txt file entitled "220111-1260 Sequence Listing_ST25" created on Aug. 16, 2019. The content of the sequence listing is incorporated herein in its entirety.

BACKGROUND

*Necrotising hepatopancreatitis* (NHP) is a bacterial disease of penaeid shrimp caused by a Gram negative, intracellular pleomorphic alpha proteobacteria initially called NHPB and it just recently classified as *Hepatobacter penaei* (Nunan et al. 2013, that belongs to the order Rickettsiales in the new family Holosporales (Leyva et al. 2018). NHP affects cultured penaeid shrimp in several countries from the Americas including the United States of America, Mexico, Belize, El Salvador, Guatemala, Honduras, Costa Rica, Nicaragua, Panama, Brazil, Colombia, Ecuador, Peru and Venezuela (OIE 2017b, Lightner, 1996, Briñez et al. 2003; Aranguren et al. 2006). It has also been reported from an African country, Eritrea (Aranguren et al. 2010). NHP is a chronic disease that causes mortalities up to 50-95% in affected post-larvae (PL) (Loy & Harris 2008), juveniles (Lightner, 1996; Johnson, 1989) and broodstock of *Penaeus vannamei* (Aranguren et al. 2006. Morales et al. 2006). The manifestation of NHP at farming level is related to particular environmental conditions such as high salinity and high temperature (Lightner 1996; Vincent & Lotz, 2007). NHP-infected shrimp show a typical soft shell, flaccid bodies, reduced feed intake and empty midguts (Lightner 1996). The acute phase lesions in diseased shrimp include necrosis and sloughing off of epithelial cells in hepatopancreas (HP) tubule, intracellular hemocytic response, and melanized HP tubules. In chronic phase, the HP lesions are characterized by atrophy of tubules, reduced epithelial cell height, low lipid storage R cells and intratubular edema (Lightner 1996). Since the first report in 1985 (Frelier et al. 1993), NHP has become such an important disease in the shrimp industry that on 2010 it was listed in the OIE-list of crustacean diseases (OIE 2017a).

Several diagnostic methods have been developed to detect and confirm *H. penaei* presence including PCR, histology and in-situ hybridization (Lightner 1996; Loy & Frelier 1996; Nunan et al. 2008; Aranguren et al. 2010) and qPCR (Vincent & Lotz 2005; Aranguren et al. 2010), however, there is only one PCR method recommended in the OIE manual (OIE 2017b) and that creates the need to have an alternative PCR and real-time PCR (qPCR) assays for *H. penaei* detection and confirmation, especially when new non-specific amplifications are being observed while screening *Artemia* cysts for *H. penaei*

Acute hepatopancreatic necrosis disease (AHPND, initially referenced to as early mortality syndrome, EMS) is also a deadly shrimp disease caused by particular *Vibrio* spp. (J. E. Han et al., 2017; Lee et al., 2015; Tran et al., 2013). This disease first emerged in China in 2009 and has rapidly spread throughout Southeast Asia to Vietnam, Malaysia, Thailand and reached Mexico in Latin America in 2013 (Nunan et al., 2014; Tran et al., 2013). The impact of AHPND in shrimp farming at global scale has been catastrophic with an estimated global loss of $1 billion per year (FAO, 2013).

SUMMARY

Described herein various PCR based assays that can detect *H. penaei* and/or *Vibrio parahaemolyticus* (*V. parahaemolyticus*) that causes AHPND in a nucleic acid sample obtained from one or more shrimp. In some aspects, the PCR based assays can detect one or more of the following genes: the flgE gene from *H. penaei*, the shrimp 18s rRNA gene, the shrimp beta actin gene from shrimp, a bacterial 16S rRNA gene from bacteria (any type of bacteria) the *Vibrio* pirA gene, and the *Vibrio* pirB gene. The assays described herein can be single assays or can be multiplexed such that more than one gene and/or more than one bacterial species can be detected in a single reaction. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

(FIG. 12A) A standard curve for the PirA gene with log linear dynamic range of 5 orders of magnitude with an R$^2$ value of 0.998, slope of −3.34 and amplification efficiency of 99.12%. (FIG. 12B) A standard curve for the PirB gene with log linear dynamic range of 6 orders of magnitude with an R$^2$ value of 0.998, slope of −3.27 and amplification efficiency of 101.92%.

DETAILED DESCRIPTION

Figure 1:
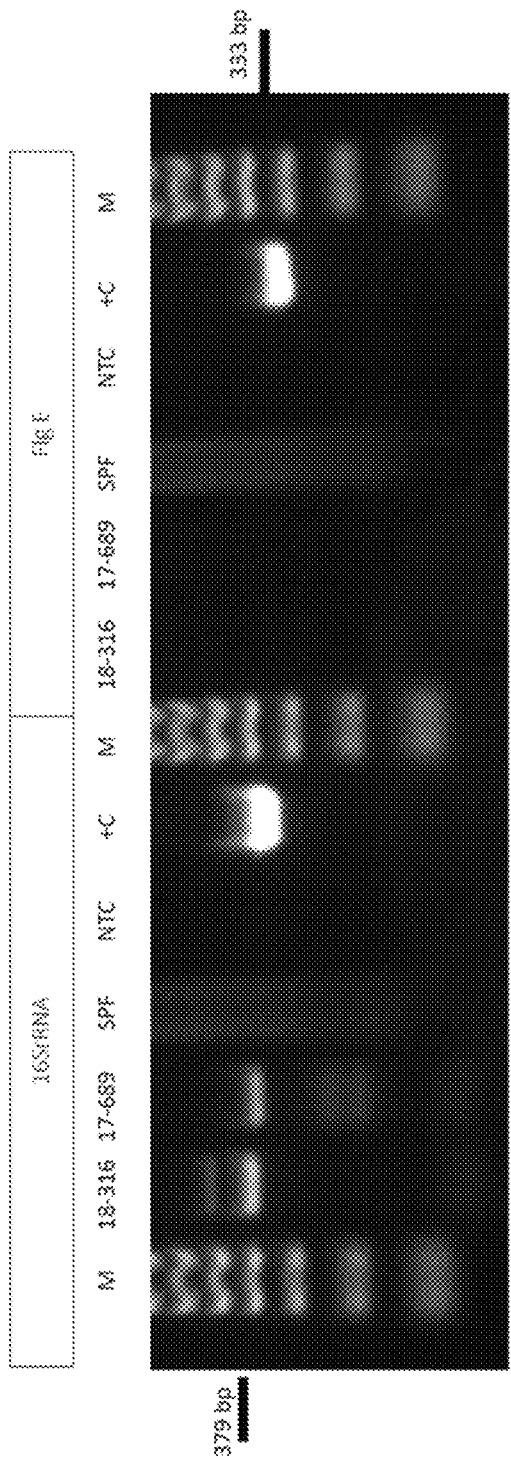
FIG. 1 shows PCR detection of *Hepatobacter penaei* (*H. penaei*) in samples of *Artemia* cysts using two different assays: 16S rRNA and flgE genes. M: 1 kb plus ladder molecular weight marker; 18-316 (case1), 17-689 (case2); NTC, Non template control; +C: *H. penaei* positive control.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "control" refers to an alternative subject or sample used in an experiment for comparison purpose and included to minimize or distinguish the effect of variables other than an independent variable.

As used herein with reference to the relationship between DNA, cDNA, cRNA, RNA, protein/peptides, and the like "corresponding to" refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" generally refers to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "DNA molecule" can include nucleic acids/polynucleotides that are made of DNA.

As used herein, the term "encode" refers to principle that DNA can be transcribed into RNA, which can then be translated into amino acid sequences that can form proteins.

As used herein, "gene" refers to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "identity," refers to a relationship between two or more nucleotide or polypeptide sequences, as determined by comparing the sequences. In the art, "identity" can also refers to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., N BLAST, and XBLAST). The default parameters are used to determine the identity for the polypeptides of the present disclosure, unless stated otherwise.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" are used interchangeably herein and generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "positive control" can refer to a "control" that is designed to produce the desired result, provided that all reagents are functioning properly and that the experiment is properly conducted.

As used herein, the term "specific binding" refers to covalent or non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

Discussion

*Necrotising hepatopancreatitis* (NHP) is a bacterial disease of penaeid shrimp caused by a Gram negative, intracellular pleomorphic alpha proteobacteria initially called NHPB and it just recently classified as *Hepatobacter penaei* (Nunan et al. 2013, that belongs to the order Rickettsiales in the new family Holosporales (Leyva et al. 2018). NHP affects cultured penaeid shrimp in several countries from the Americas including the United States of America, Mexico, Belize, El Salvador, Guatemala, Honduras, Costa Rica, Nicaragua, Panama, Brazil, Colombia, Ecuador, Peru and Venezuela (OIE 2017b, Lightner, 1996, Briñez et al. 2003; Aranguren et al. 2006). It has also been reported from an African country, Eritrea (Aranguren et al. 2010). NHP is a chronic disease that causes mortalities up to 50-95% in affected post-larvae (PL) (Loy & Harris 2008), juveniles (Lightner, 1996; Johnson, 1989) and broodstock of *Penaeus vannamei* (Aranguren et al. 2006. Morales et al. 2006). The manifestation of NHP at farming level is related to particular environmental conditions such as high salinity and high temperature (Lightner 1996; Vincent & Lotz, 2007). NHP-infected shrimp show a typical soft shell, flaccid bodies, reduced feed intake and empty midguts (Lightner 1996). The acute phase lesions in diseased shrimp include necrosis and sloughing off of epithelial cells in hepatopancreas (HP) tubule, intracellular hemocytic response, and melanized HP tubules. In chronic phase, the HP lesions are characterized by atrophy of tubules, reduced epithelial cell height, low lipid storage R cells and intratubular edema (Lightner 1996). Since the first report in 1985 (Frelier et al. 1993), NHP has become such an important disease in the shrimp industry that on 2010 it was listed in the OIE-list of crustacean diseases (OIE 2017a).

Several diagnostic methods have been developed to detect and confirm *H. penaei* presence including PCR, histology and in-situ hybridization (Lightner 1996; Loy & Frelier 1996; Nunan et al. 2008; Aranguren et al. 2010) and qPCR (Vincent & Lotz 2005; Aranguren et al. 2010), however, there is only one PCR method recommended in the OIE manual (OIE 2017b) and that creates the need to have an alternative PCR and real-time PCR (qPCR) assays for *H. penaei* detection and confirmation, especially when new non-specific amplifications are being observed while screening *Artemia* cysts for *H. penaei*

Acute hepatopancreatic necrosis disease (AHPND, initially referenced to as early mortality syndrome, EMS) is also a deadly shrimp disease caused by particular *Vibrio* spp. (J. E. Han et al., 2017; Lee et al., 2015; Tran et al., 2013). This disease first emerged in China in 2009 and has rapidly spread throughout Southeast Asia to Vietnam, Malaysia, Thailand and reached Mexico in Latin America in 2013 (Nunan et al., 2014; Tran et al., 2013). The impact of AHPND in shrimp farming at global scale has been catastrophic with an estimated global loss of $1 billion per year (FAO, 2013).

The pathogenic *Vibrio* spp. harbors a large plasmid that ranges from 69-74 kb, on average of 33 copies per cell, and contains *Photorhabdus* Insect-Related (Pir) toxin genes PirA and PirB (J. E. Han et al., 2017, 2015; Yang et al., 2014). The binary toxin PirAB has been confirmed to be as the etiological agent factor for AHPND (J. Han et al., 2015). To date, two PCR based methods have been reported to detect both toxins genes PirA and PirB, a duplex PCR reported by J. E. Han et al., (2017) and the two-tube nested AP4 PCR developed by Dangtip et al., (2015). For quantification and detection, a qPCR assay that detects PirA has been reported but does not detect type II mutants (J. E. Han et al., 2015). The detection of both types of mutants is fundamental for the study of plasmid transmission dynamics and recording the presence of the virulence plasmid since studies by Lee et al., (2015) that suggest that the PirA and PirB genes may be lost or acquired by horizontal gene transfer via transposition or homologous recombination.

With that said, described herein various PCR based assays that can detect *H. penaei* and/or *Vibrio parahaemolyticus* (*V. parahaemolyticus*) that causes AHPND in a nucleic acid sample obtained from one or more shrimp. In some aspects, the PCR based assays can detect one or more of the following genes: the flgE gene from *H. penaei*, the shrimp 18s rRNA gene, the shrimp beta actin gene from shrimp, a bacterial 16S rRNA gene from bacteria (any type of bacteria) the *Vibrio* pirA gene, and the *Vibrio* pirB gene. The assays described herein can be single assays or can be multiplexed such that more than one gene and/or more than one bacterial species can be detected in a single reaction. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays to Detect *H. penaei* and/or *V. parahaemolyticus* in Shrimp

Assays to Detect *H. penaei*

Described herein are PCR-based assays that can be capable of detecting *H. penaei* from a nucleotide sample obtained from one or more shrimp. In some embodiments, the sample is from hepatopancreas. Methods of harvesting, collecting, extracting and otherwise preparing an appropriate nucleic acid sample from shrimp for analysis by polymerase chain reaction will be appreciated by one of ordinary skill in the art in view of this disclosure. DNA extraction from hepatopancreas samples can be carried out using a commercial method. For example, DNA extraction can be carried out using a Maxwell® 16 Cell LEV DNA Purification Kit. Other suitable commercial reagents, kits, and methods will be appreciated by one of ordinary skill in the art in view of this description herein. The nucleic acid sample can contain, for example, genomic DNA, cDNA, and/or RNA. After obtaining the nucleic acid sample, the flgE gene from *H. penaei* can be detected by performing a PCR based assay. The PCR based assay can employ an appropriate primer set to amplify an amplicon specific to the flgE gene from *H. penaei*. The PCR based assay can also employ appropriate primer sets to amplify one or more reaction and assay control genes, such as a shrimp housekeeping gene (e.g. beta actin or 18S rRNA). The PCR based assay can also employ a primer sets to amplify a bacterial control gene (e.g. a 16s rRNA gene). The PCR method employed can be any appropriate PCR method, such as standard PCR and real-time PCR (both quantitative and qualitative).

In some embodiments, such as those employing real-time PCR methods of gene fragment amplification, an oligonucleotide probe specific to the gene and primer set can be used. An example of such a probe is a Taqman® probe. Different genes can be detected in the same reaction using Taqman® probes by using a different fluorophore on each probe so that the gene amplification from each gene can be differentiated based on the fluorescence produced. Quencher molecules can be fluorescent (e.g., TAMRA™) or nonfluorescent molecules e.g. DABCYL and Black Hole Quencher®). Example fluorophores include, but are not limited to 6-FAM™, JOE™, TET™, Cal Fluor® Gold 540, HEX™, Cal Fluor® Orange 560, TAMRA™, VIC™, Cyanine 3, Quasar® 570, Cal Fluor® Orange 590, ROX™, Texas Red®, Cyanine 5, Quasar® 670, and Cyanine 5.5.

In some embodiments, such as those employing real-time PCR, PCR methods of gene fragment amplification, a fluorescent dye that binds to double stranded DNA can be used to monitor gene fragment amplification during each PCR reaction cycle. An example of such a dye is SYBR® Green and its variants. In assays where multiple genes are amplified in a single reaction where a fluorescent dye that binds to double stranded DNA is used to monitor amplification of gene fragments, the amount (relative or quantitative) of gene fragments amplified from the different genes present in the reaction can be distinguished from each other by virtue of different melting curves. Primer sets can be designed for each gene in the multiplex reaction such that the gene fragment generated will disassociate at a different temperature and thus produce a different melting curve.

As such, the PCR-based assays (single or multiplexed reactions) described herein that can be capable of detecting *H. penaei* infection in a shrimp or population thereof can be configured to detect one or more of the following genes: the flgE from *H penaei*, a shrimp beta actin gene, and/or a shrimp 18S rRNA gene.

In some embodiments, an assay to detect *Hepatobacter penaei* (*H. penaei*) infection in shrimp can include the steps of amplifying a fragment of the flgE gene of *H. penaei* using a polymerase chain reaction (PCR) method, wherein the step of amplifying includes contacting a nucleic acid sample obtained from one or more shrimp with a first oligonucleotide primer and a second oligonucleotide primer, wherein the first oligonucleotide primer is a forward direction oligonucleotide primer adapted for PCR amplification of a fragment of the flgE gene of *H. penaei* with the second oligonucleotide primer and specifically binds a region of the flgE gene of *H. penaei*, wherein the second oligonucleotide primer is a reverse direction oligonucleotide primer adapted for PCR amplification of a fragment of the flgE gene of *H. penaei* with the first oligonucleotide primer and specifically binds a region of the flgE gene of *H. penaei*; and the step of detecting the presence or absence of an amplified double stranded DNA fragment of the flgE gene in the nucleic acid sample. In some embodiments, the step of detection can occur during the step of amplifying. In other words, the fragment is amplified and detected in real-time. This is also referred to in the art as real-time PCR.

The step of amplifying can further include contacting the nucleic acid sample with a first oligonucleotide probe adapted for real-time PCR amplification and detection, wherein the first oligonucleotide probe specifically binds a region of the flgE gene that is between the region of the flgE gene where the first oligonucleotide primer specifically binds and the region of the flgE gene where the second oligonucleotide primer specifically binds, and wherein the first oligonucleotide probe is coupled to a fluorophore and a quencher molecule. The fluorophore of the first oligonucleotide probe is released during the step of amplifying and produces detectable fluorescence.

The step of amplifying can further include contacting the nucleic acid sample with a third oligonucleotide primer and a fourth oligonucleotide primer, wherein the third oligonucleotide primer is a forward direction oligonucleotide primer adapted for PCR amplification of a fragment of the beta actin gene or the 18S rRNA gene of shrimp with the fourth oligonucleotide primer and specifically binds a region of the beta actin gene or the 18S rRNA gene of shrimp, wherein the fourth oligonucleotide primer is a reverse direction oligonucleotide primer adapted for PCR amplification of a fragment of the beta actin gene or the 18S rRNA gene of shrimp with the third oligonucleotide primer and specifically binds a region of the beta actin gene or the 18S rRNA gene of shrimp, and wherein the step of detecting further includes detecting the presence or absence of an amplified double stranded DNA fragment of the beta actin gene or the 18S rRNA gene of shrimp in the nucleic acid sample.

In some embodiments, the step of amplifying the flE gene fragment and the step of amplifying the beta actin gene or the 18S rRNA gene of shrimp can be carried out in the same PCR reaction. In some embodiments, the step of amplifying the flgE gene fragment and the step of amplifying the beta actin gene or the 18S rRNA gene of shrimp is carried out in the different PCR reactions.

The step of amplifying can further include contacting the nucleic acid sample with a second oligonucleotide probe adapted for real-time PCR amplification and detection, wherein the second oligonucleotide probe specifically binds a region of the beta actin gene or the 18S rRNA gene of shrimp that is between the region of the beta actin gene or the 18S rRNA gene of shrimp where the third oligonucleotide primer specifically binds and the region of the beta actin gene or 18S rRNA gene of shrimp gene where the fourth oligonucleotide primer specifically binds, and wherein the second oligonucleotide probe is coupled to a fluorophore and a quencher molecule. The fluorophore of the second oligonucleotide probe can be released during the step of amplifying and produces detectable fluorescence. The fluorophore of the second oligonucleotide probe can be different from the fluorophore of the first oligonucleotide probe.

The step of amplifying can further include comprises contacting the amplified double stranded DNA fragment of the flgE gene, the beta actin gene, the 18S rRNA gene of shrimp, or any combination thereof with a detectable dye molecule that binds double stranded DNA. The step of contacting the amplified double stranded DNA fragment of the flgE gene, the beta actin gene, the 18S rRNA gene of shrimp, or any combination thereof with a detectable dye molecule that binds double stranded DNA can occur during the step of amplifying. In these embodiments, as the fragments are produced during each PCR cycle, the detectable dye molecule(s) are associated or otherwise integrated with the double stranded DNA fragments being produced.

The first oligonucleotide primer has a sequence according to SEQ ID NO: 1 or 3. The second oligonucleotide primer has a sequence according to SEQ ID NO: 2 or 4. The third primer has a sequence according to SEQ ID NO: 14. The fourth primer has a sequence according to SEQ ID NO.: 15. The first oligonucleotide probe can include a sequence according to SEQ ID NO: 5.

The assay can also include the step of treating the shrimp for *H. penaei* infection if a population is determined to be infected. In some aspects, the step of treating the shrimp can include the step of administering an amount of an antibiotic to the shrimp or a population of shrimp that the sampled shrimp was obtained from. It will be appreciated that the assay may require that some shrimp of a population may be sacrificed to obtain a sample. As such, the sample can include a number of shrimp that can be an appropriate indicator of the population at large. In some aspects the antibiotic can be oxyetracycline and/or forfenicol.

In some aspects, the assay can be used to determine the efficacy of candidate therapeutic compounds. In these aspects, a population of shrimp that can have one or more shrimp infected with *H. penaei* can be administered an amount of a candidate therapeutic compound. An assay for *H. penaei* as described herein can be performed to determine if the candidate therapeutic compound is effective to treat *H. penaei* infections. In some aspects, the assay can be performed before and/or after administration of the candidate therapeutic compound.

Assays to Detect *V. parahaemolyticus*

Described herein are PCR-based assays that can be capable of detecting *V. parahaemolyticus* from a nucleotide sample obtained from one or more shrimp. The sample can be a hepatopancreas tissue and/or *Artemia* cyst sample. Methods of harvesting, collecting, extracting and otherwise preparing an appropriate nucleic acid sample from shrimp for analysis by polymerase chain reaction will be appreciated by one of ordinary skill in the art in view of this disclosure. DNA extraction from hepatopancreas tissue and/or *Artemia* cyst samples can be carried out using a commercial method. For example, DNA extraction can be carried out using a Maxwell® 16 Cell LEV DNA Purification Kit. The nucleic acid sample can contain, for example, genomic DNA, cDNA, and/or RNA. After obtaining the nucleic acid sample, the pirA gene from *V. parahaemolyticus*, the piRB, gene from *V. parahaemolyticus*, the 16S rRNA gene from *V. parahaemolyticus*, 18S rRNA from shrimp, the beta actin gene from shrimp, or any combination thereof can be detected by performing a PCR based assay. The PCR based assay can employ an appropriate primer set(s) to amplify an amplicon(s) specific to the pirA gene from *V. parahaemolyticus*, the piRB, gene from *V. parahaemolyticus*, the 16S rRNA gene from *V. parahaemolyticus*, 18S rRNA from shrimp, or any combination thereof. As previously mentioned, the PCR based assay can also employ appropriate primer sets to amplify one or more reaction and assay control genes, such as a shrimp housekeeping gene (e.g. 18S rRNA). The PCR based assay can also employ a primer sets to amplify a bacterial control gene (e.g. 16s rRNA gene). The PCR method employed can be any appropriate PCR method, such as standard PCR and real-time PCR (both quantitative and qualitative).

In some embodiments, such as those employing real-time PCR methods of gene fragment amplification, an oligonucleotide probe specific to the gene and primer set can be used. An example of such a probe is a Taqman® probe. Different genes can be detected in the same reaction using Taqman® probes by using a different fluorophore on each probe so that the gene amplification from each gene can be differentiated based on the fluorescence produced. Suitable fluorophores and quencher molecules will be appreciated by those of skill in the art. Quencher molecules can be fluorescent (e.g., TAMRA™) or nonfluorescent molecules e.g. DABCYL and Black Hole Quencher®). Example fluorophores include, but are not limited to 6-FAM™, JOE™, TET™, Cal Fluor® Gold 540, HEX™, Cal Fluor® Orange 560, TAMRA™, VIC™, Cyanine 3, Quasar® 570, Cal Fluor® Orange 590, ROX™, Texas Red®, Cyanine 5, Quasar® 670, and Cyanine 5.5.

In some embodiments, such as those employing real-time PCR, PCR methods of gene fragment amplification, a fluorescent dye that binds to double stranded DNA can be used to monitor gene fragment amplification during each PCR reaction cycle. An example of such a dye is SYBR® Green and its variants. In assays where multiple genes are amplified in a single reaction where a fluorescent dye that binds to double stranded DNA is used to monitor amplification of gene fragments, the amount (relative or quantitative) of gene fragments amplified from the different genes present in the reaction can be distinguished from each other by virtue of different melting curves. Primer sets can be designed for each gene in the multiplex reaction such that the gene fragment generated will disassociate at a different temperature and thus produce a different melting curve.

As such, the PCR-based assays (single or multiplexed reactions) described herein that can be capable of detecting *V. parahaemolyticus* infection in a shrimp or population thereof can be configured to detect the pirA gene from *V. parahaemolyticus*, the piRB, gene from *V. parahaemolyticus*, the 16S rRNA gene from *V. parahaemolyticus*, 18S rRNA or Beta actin from shrimp, or any combination thereof.

In some embodiments, an assay to detect *Vibrio parahaemolyticus* (*V. parahaemolyticus*) in shrimp can include the steps of amplifying a fragment of the pirA gene and/or the pirB gene of *V. parahaemolyticus* using a polymerase chain reaction (PCR) method, wherein the step of amplifying includes contacting a nucleic acid sample obtained from one or more shrimp with a first oligonucleotide primer and a second oligonucleotide primer and/or a third oligonucleotide primer and a further oligonucleotide primer, wherein the first oligonucleotide primer is a forward direction oligonucleotide primer adapted for PCR amplification of a fragment of the pirA gene of *V. parahaemolyticus* with the second oligonucleotide primer and specifically binds a region of the pirA gene of *V. parahaemolyticus*, wherein the second oligonucleotide primer is a reverse direction oligonucleotide primer adapted for PCR amplification of a fragment of the pirA gene of *V. parahaemolyticus* with the first oligonucleotide primer and specifically binds a region of the pirA gene of *V. parahaemolyticus*, wherein the third oligonucleotide primer is a forward direction oligonucleotide primer adapted for PCR amplification of a fragment of the pirB gene of *V. parahaemolyticus* with the fourth oligonucleotide primer and specifically binds a region of the pirB gene of *V. parahaemolyticus*, wherein the fourth oligonucleotide primer is a reverse direction oligonucleotide primer adapted for PCR amplification of a fragment of the pirB gene of *V. parahaemolyticus* with the third oligonucleotide primer and specifically binds a region of the pirB gene of *V. parahaemolyticus*; and detecting the presence or absence of an amplified double stranded DNA fragment of the pirA gene and/or the pirB gene of *V. parahaemolyticus* in the nucleic acid sample.

The step of amplifying further can further include contacting the nucleic acid sample with a fifth oligonucleotide primer and a sixth oligonucleotide primer, wherein the fifth oligonucleotide primer is a forward direction oligonucleotide primer adapted for PCR amplification of a fragment of the 16S rRNA gene of *V. parahaemolyticus* with the sixth oligonucleotide primer and specifically binds a region of the 16S rRNA gene of *V. parahaemolyticus*, wherein the sixth oligonucleotide primer is a reverse direction oligonucleotide primer adapted for PCR amplification of a fragment of the 16S rRNA gene of *V. parahaemolyticus* with the fifth oligonucleotide primer and specifically binds a region of the 16S rRNA gene of *V. parahaemolyticus*, and wherein the step of detecting further includes detecting the presence or absence of an amplified double stranded DNA fragment of the 16S rRNA gene of *V. parahaemolyticus* in the nucleic acid sample.

The step of amplifying further can further include contacting the nucleic acid sample with a seventh oligonucleotide primer and an eighth oligonucleotide primer, wherein the seventh oligonucleotide primer is a forward direction oligonucleotide primer adapted for PCR amplification of a fragment of the housekeeping gene (e.g. 18S rRNA gene) of shrimp with the eighth oligonucleotide primer and specifically binds a region of the housekeeping gene (e.g. 18S rRNA gene) of shrimp, wherein the eighth oligonucleotide primer is a reverse direction oligonucleotide primer adapted for PCR amplification of a fragment of the housekeeping gene (e.g. the 18S rRNA gene) of shrimp with the seventh oligonucleotide primer and specifically binds a region of housekeeping gene (e.g. the 18S rRNA gene) of shrimp, and wherein the step of detecting further includes detecting the presence or absence of an amplified double stranded DNA fragment of the beta actin gene or the 18S rRNA gene of shrimp in the nucleic acid sample.

The step of amplifying can include contacting the nucleic acid sample with a first oligonucleotide probe and/or a second oligonucleotide probe adapted for real-time PCR amplification and detection, wherein the first oligonucleotide probe specifically binds a region of the pirA gene that is between the region of the pirA gene where the first oligonucleotide primer specifically binds and the region of the pirA gene where the second oligonucleotide primer specifically binds, wherein the second oligonucleotide probe specifically binds a region of the pirB gene that is between the region of the pirB gene where the third oligonucleotide primer specifically binds and the region of the pirB gene where the fourth oligonucleotide primer specifically binds, and wherein the first and the second oligonucleotide probes are each coupled to a fluorophore and a quencher molecule. The fluorophore of the first oligonucleotide probe and/or the second oligonucleotide probe can be released during the step of amplifying and produce(s) detectable fluorescence. The fluorophore of the first oligonucleotide probe can be different from the fluorophore of the second oligonucleotide probe.

The step of amplifying can include contacting the nucleic acid sample with a third oligonucleotide probe adapted for real-time PCR amplification and detection, wherein the third oligonucleotide probe specifically binds a region of the 16S rRNA gene of *V. parahaemolyticus* that is between the region of the 16S rRNA gene of *V. parahaemolyticus* where the fifth oligonucleotide primer specifically binds and the region of the 16S rRNA gene of *V. parahaemolyticus* where the sixth oligonucleotide primer specifically binds, and wherein the third oligonucleotide probe is coupled to a fluorophore and a quencher molecule. The fluorophore of the third oligonucleotide probe can be released during the step of amplifying and produces detectable fluorescence. The fluorophore of the third oligonucleotide probe can be different from the fluorophore of the first and the second oligonucleotide probes.

The step of amplifying can include contacting the nucleic acid sample with a fourth oligonucleotide probe adapted for real-time PCR amplification and detection, wherein the fourth oligonucleotide probe specifically binds a region of the beta actin gene or the 18S rRNA gene of shrimp that is between the region of the beta actin gene or the 18S rRNA gene of shrimp where the seventh oligonucleotide primer specifically binds and the region of the beta actin gene or the 18S rRNA gene of shrimp where the eighth oligonucleotide primer specifically binds, and wherein the fourth oligonucleotide probe is coupled to a fluorophore and a quencher molecule. The fluorophore of the fourth oligonucleotide probe is released during the step of amplifying and produces detectable fluorescence. The fluorophore of the third oligonucleotide probe is different from the fluorophore of the first, the second, and the third oligonucleotide probes.

The step of amplifying can include contacting an amplified double stranded DNA fragment of pirA gene, the pirB gene, the 16s rRNA gene of *V. parahaemolyticus*, the beta actin gene of shrimp, the 18S rRNA gene of shrimp, or any combination thereof with a detectable dye molecule that binds double stranded DNA. The step of contacting the amplified double stranded DNA fragment of pirA gene, the pirB gene, the 16s rRNA gene of *V. parahaemolyticus*, the shrimp housekeeping gene (e.g. the 18S rRNA gene of shrimp) or any combination thereof with a detectable dye molecule that binds double stranded DNA can occur during amplification.

In some embodiments, the first oligonucleotide primer can have a sequence according to SEQ ID NO: 8. The second oligonucleotide primer can have a sequence according to SEQ ID NO: 9. The third oligonucleotide primer can have a sequence according to SEQ ID NO: 10. The fourth oligonucleotide primer can have a sequence according to SEQ ID NO: 11. The fifth oligonucleotide primer can have a sequence according to SEQ ID NO: 12. The sixth oligonucleotide primer can have a sequence according to SEQ ID NO: 13. The seventh oligonucleotide primer can have a sequence according to SEQ ID NO 14. The eighth oligonucleotide primer can have a sequence according to SEQ ID NO: 15.

The assay can also include the step of treating the shrimp for *V. parahaemolyticus* infection if a population is determined to be infected. In some aspects, the step of treating the shrimp can include the step of administering an amount of a lytic bacteriophage (e.g. A3S and Vpms1) to the shrimp or a population of shrimp that the sampled shrimp was obtained from. In some aspects, the step of treating the shrimp can include the step of administering an amount of an organic acid to the shrimp or a population of shrimp that the sampled shrimp was obtained from. In some aspects, the step of treating the shrimp can include the step of administering an amount of an antimicrobial to the shrimp or a population of shrimp that the sampled shrimp was obtained from. The antimicrobial can be ampicillin, gentamicin, neomycin, cephalothin, tetracycline, nalidixic acid, kanamycin, chloramphenicol, streptomycin, or any combination thereof. In some aspects, the step of treating the shrimp can include the step of subjecting the shrimp or a population of shrimp that the sampled shrimp was obtained from to acidic electrolyzed water treatment. In some aspects, the step of treating the shrimp can include the step of administering an amount of a probiotic to the shrimp or a population of shrimp that the sampled shrimp was obtained from. It will be appreciated that the assay may require that some shrimp of a population may be sacrificed to obtain a sample. As such, the sample can include a number of shrimp that can be an appropriate indicator of the population at large.

In some aspects, the assay can be used to determine the efficacy of candidate therapeutic compounds. In these aspects, a population of shrimp that can have one or more shrimp infected with *V. parahaemolyticus* can be administered an amount of a candidate therapeutic compound. An assay for *V. parahaemolyticus* as described herein can be performed to determine if the candidate therapeutic compound is effective to treat *V. parahaemolyticus* infections. In some aspects, the assay can be performed before and/or after administration of the candidate therapeutic compound.

Assays to detect *H. penaei* and *V. parahaemolyticus*

Described herein are PCR-based assays that can be capable of detecting *H. penaei* and *V. parahaemolyticus* in a nucleotide sample obtained from one or more shrimp. In some Methods of harvesting, collecting, extracting and otherwise preparing an appropriate nucleic acid sample from shrimp for analysis by polymerase chain reaction will be appreciated by one of ordinary skill in the art in view of this disclosure. DNA extraction was carried out from hepatopancreas (HP) and *Artemia* cysts. Approximately 25-50 mg of hepatopancreas tissue and/or *Artemia* cysts can be used for DNA extraction using commercially available reagents and/or kits (e.g. a Maxwell® 16 Cell LEV DNA Purification Kit). The nucleic acid sample can contain, for example, genomic DNA, cDNA, and/or RNA. After obtaining the nucleic acid sample, the flgE gene from *H. penaei*, the pirA gene from *V. parahaemolyticus*, the piRB, gene from *V. parahaemolyticus*, the 16S rRNA gene from *V. parahaemolyticus*, 18S rRNA from shrimp, the beta actin gene from shrimp, or any combination thereof can be detected by performing a PCR based assay. The PCR based assay can employ an appropriate primer set(s) to amplify an amplicon(s) specific to the flgE gene from *H. penaei*, the pirA gene from *V. parahaemolyticus*, the piRB, gene from *V. parahaemolyticus*, the 16S rRNA gene from *V. parahaemolyticus*, 18S rRNA from shrimp, the beta actin gene from shrimp, or any combination thereof. As previously mentioned, the PCR based assay can also employ appropriate primer sets to amplify one or more reaction and assay control genes, such as a shrimp housekeeping gene (e.g. beta actin or 18S rRNA). The PCR based assay can also employ a primer sets to amplify a control gene (e.g. a 16s rRNA gene). The PCR method employed can be any appropriate PCR method, such as standard PCR and real-time PCR (both quantitative and qualitative).

As is described in greater detail elsewhere herein, the reagents (e.g. primer and/or probe sets) to detect multiple genes can be included in a single reaction. In the assay to detect both *H. penaei*, and *V. parahaemolyticus*, a single PCR reaction can include primer sets and/or probes to detect at last one gene specific to *H. penaei* and one gene specific to *V. parahaemolyticus*. In some embodiments, a PCR reaction can contain primer sets and/or probes to detect flgE from *H. penaei* and pirA and pirB from *V. parahaemolyticus*. The reactions can also contain various primer sets to detect control genes such as 16s rRNA from *V. parahaemolyticus*, shrimp beta actin, shrimp 18s rRNA, or any combination thereof. As such, the PCR-based assays (single or multiplexed reactions) described herein that can be capable of detecting *V. parahaemolyticus* infection in a shrimp or population thereof can be configured to detect the flgE gene from *H. penaei*, the pirA gene from *V. parahaemolyticus*, the piRB, gene from *V. parahaemolyticus*, the 16S rRNA gene from *V. parahaemolyticus,* 18S rRNA from shrimp, the beta actin gene from shrimp, or any combination thereof.

In some embodiments, such as those employing real-time PCR methods of gene fragment amplification, an oligonucleotide probe specific to the gene and primer set can be used. An example of such a probe is a Taqman® probe. Different genes can be detected in the same reaction using Taqman® probes by using a different fluorophore on each probe so that the gene amplification from each gene can be differentiated based on the fluorescence produced. Suitable fluorophores and quencher molecules will be appreciated by those of skill in the art. Quencher molecules can be fluorescent (e.g., TAMRA™) or nonfluorescent molecules e.g. DABCYL and Black Hole Quencher®). Example fluorophores include, but are not limited to 6-FAM™, JOE™, TET™, Cal Fluor® Gold 540, HEX™, Cal Fluor® Orange 560, TAMRA™, VIC™, Cyanine 3, Quasar® 570, Cal Fluor® Orange 590, ROX™, Texas Red®, Cyanine 5, Quasar® 670, and Cyanine 5.5.

In some embodiments, such as those employing real-time PCR, PCR methods of gene fragment amplification, a fluorescent dye that binds to double stranded DNA can be used to monitor gene fragment amplification during each PCR reaction cycle. An example of such a dye is SYBR® Green and its variants. In assays where multiple genes are amplified in a single reaction where a fluorescent dye that binds to double stranded DNA is used to monitor amplification of gene fragments, the amount (relative or quantitative) of gene fragments amplified from the different genes present in the reaction can be distinguished from each other by virtue of different melting curves. Primer sets can be designed for each gene in the multiplex reaction such that the gene fragment generated will disassociate at a different temperature and thus produce a different melting curve.

Specific assays for the various genes discussed in this section are described elsewhere herein.

The assay can also include the step of treating the shrimp for *V. parahaemolyticus* and/or *H. penaei* infection if a population is determined to be infected. In some aspects, the step of treating the shrimp can include the step of administering an amount of a lytic bacteriophage (e.g. A3S and Vpms1) to the shrimp or a population of shrimp that the sampled shrimp was obtained from. In some aspects, the step of treating the shrimp can include the step of administering an amount of an organic acid to the shrimp or a population of shrimp that the sampled shrimp was obtained from. In some aspects, the step of treating the shrimp can include the step of administering an amount of an antimicrobial to the shrimp or a population of shrimp that the sampled shrimp was obtained from. The antimicrobial can be ampicillin, gentamicin, neomycin, cephalothin, tetracycline, nalidixic acid, kanamycin, chloramphenicol oxyetracycline, forfenicol and streptomycin, or any combination thereof. In some aspects, the step of treating the shrimp can include the step of subjecting the shrimp or a population of shrimp that the sampled shrimp was obtained from to acidic electrolyzed water treatment. In some aspects, the step of treating the shrimp can include the step of administering an amount of a probiotic to the shrimp or a population of shrimp that the sampled shrimp was obtained from. It will be appreciated that the assay may require that some shrimp of a population may be sacrificed to obtain a sample. As such, the sample can include a number of shrimp that can be an appropriate indicator of the population at large.

In some aspects, the assay can be used to determine the efficacy of candidate therapeutic compounds. In these aspects, a population of shrimp that can have one or more shrimp infected with *V. parahaemolyticus* and/or *H. penaei* can be administered an amount of a candidate therapeutic compound. An assay for *V. parahaemolyticus* and/or *H. penaei* as described herein can be performed to determine if the candidate therapeutic compound is effective to treat *V. parahaemolyticus* and/or *H. penaei* infections. In some aspects, the assay can be performed before and/or after administration of the candidate therapeutic compound.

Kits for Detecting *H. penaei* and/or *V. parahaemolyticus*

Also provided herein are kits that can be used to detect *H. penaei* and/or *V. parahaemolyticus*. The kits can include one or more primer sets and/or probes that can be used to amplify and detect the flgE gene from *H. penaei*, the pirA gene from *V. parahaemolyticus*, the piRB, gene from *V. parahaemolyticus*, the 16S rRNA gene from *V. parahaemolyticus*, a shrimp housekeeping gene (e.g. the 18S rRNA gene from shrimp), or any combination thereof. The kits can also contain one or more reagents need to perform a PCR-based reaction including but not limited to, nucleotides, a polymerase (e.g. a Taq polymerase), buffers, salts, preservatives, dyes, etc. In some aspects, an amount of SYBR Green or a variant thereof is provided in the Kit.

In some embodiments the kit does not include primer and/or probe sets capable of detecting *H. panaei*. In some embodiments, these kits only include primer and/or probe sets capable of detecting *V. parahaemolyticus* and control genes. In some embodiments, the kit does not include primer and/or probe sets capable of detecting *V. parahaemolyticus*. In some embodiments, these kits only include primer and/or probe sets capable of detecting *H. panaei* and control genes. In some embodiments, the kit includes primer and/or probe sets capable of detecting both *H. panaei* and *V. parahaemolyticus*. These kits can also include primer and/or probe sets capable of detecting control genes. The genes specific to both *H. panaei* or *V. parahaemolyticus* as well as control genes are discussed and described elsewhere herein.

In some embodiments, the kit can include a first primer pair adapted for PCR, wherein the first primer pair comprises a first oligonucleotide primer and a second oligonucleotide primer, wherein the first oligonucleotide primer is a forward direction oligonucleotide primer adapted for PCR amplification of a fragment of the flgE gene of *H. penaei* with the second oligonucleotide primer and specifically binds a region of the flgE gene of *H. penaei*, and wherein the second oligonucleotide primer is a reverse direction oligonucleotide primer adapted for PCR amplification of a fragment of the flgE gene of *H. penaei* with the first oligonucleotide primer and specifically binds a region of the flgE gene of *H. penaei*. The kit can further include a second primer pair adapted for PCR, wherein the second primer pair comprises a third oligonucleotide primer and a fourth oligonucleotide primer, wherein the third oligonucleotide primer is a forward direction oligonucleotide primer adapted for PCR amplification of a fragment of the beta actin gene or the 18S rRNA gene of shrimp with the fourth oligonucleotide primer and specifically binds a region of the beta actin gene or the 18S rRNA gene of shrimp, and wherein the second oligonucleotide primer is a reverse direction oligonucleotide primer adapted for PCR amplification of a fragment of the beta actin gene or the 18S rRNA gene of shrimp with the third oligonucleotide primer and specifically binds a region of the beta actin gene or the 18S rRNA gene of shrimp.

The kit can further include a third primer pair adapted for PCR and/or a fourth primer pair adapted for PCR, wherein the third primer pair comprises a fifth oligonucleotide primer and a sixth oligonucleotide primer, wherein the fifth oligonucleotide primer is a forward direction oligonucleotide primer adapted for PCR amplification of a fragment of the pirA gene of *V. parahaemolyticus* with the sixth oligonucleotide primer and specifically binds a region of the pirA gene of *V. parahaemolyticus*, and wherein the sixth oligonucleotide primer is a reverse direction oligonucleotide primer adapted for PCR amplification of a fragment of the pirA gene of *V. parahaemolyticus* with the fifth oligonucleotide primer and specifically binds a region of the pirA gene of *V. parahaemolyticus*, and wherein the fourth primer pair comprises a seventh oligonucleotide primer and an eighth oligonucleotide primer, wherein the seventh oligonucleotide primer is a forward direction oligonucleotide primer adapted for PCR amplification of a fragment of the pirB gene of *V. parahaemolyticus* with the eighth oligonucleotide primer and specifically binds a region of the pirB gene of *V. parahaemolyticus* and wherein the eighth oligonucleotide primer is a reverse direction oligonucleotide primer adapted for PCR amplification of a fragment of the pirB gene of *V. parahaemolyticus* with the seventh oligonucleotide primer and specifically binds a region of the pirB gene of *V. parahaemolyticus*.

The kit can further include a fifth primer pair adapted for PCR, wherein the fifth primer pair comprises a ninth oligonucleotide primer and a tenth oligonucleotide primer, wherein the ninth oligonucleotide primer is a forward direction oligonucleotide primer adapted for PCR amplification of a fragment of the 16S rRNA gene of *V. parahaemolyticus* with the tenth oligonucleotide primer and specifically binds a region of the 16S rRNA gene of *V. parahaemolyticus*, and wherein the tenth oligonucleotide primer is a reverse direction oligonucleotide primer adapted for PCR amplification of a fragment of the 16S rRNA gene of *V. parahaemolyticus* with the ninth oligonucleotide primer and specifically binds a region of the 16S rRNA gene of *V. parahaemolyticus*.

The kit can include a first oligonucleotide probe adapted for real-time PCR, wherein the first oligonucleotide probe specifically binds a region of the flgE gene that is between the region of the flgE gene where the first oligonucleotide primer specifically binds and the region of the flgE gene where the second oligonucleotide primer specifically binds, wherein the first oligonucleotide probe is coupled to a fluorophore and a quencher molecule.

The kit can include second oligonucleotide probe, wherein the second oligonucleotide probe specifically binds a region of the beta actin gene or the 18S rRNA gene of shrimp that is between the region of the beta actin gene or the 18S rRNA gene of shrimp where the third oligonucleotide primer specifically binds and the region of the beta actin gene or the 18S rRNA gene of shrimp gene where the fourth oligonucleotide primer specifically binds, wherein the second oligonucleotide probe is coupled to a fluorophore and a quencher molecule. The fluorophore of the first oligonucleotide probe can be different from the fluorophore of the second oligonucleotide probe.

The kit can include a third and/or fourth oligonucleotide probe, a third oligonucleotide probe and/or a fourth oligonucleotide probe adapted for real-time PCR amplification and detection, wherein the third oligonucleotide probe specifically binds a region of the pirA gene that is between the region of the pirA gene where the fifth oligonucleotide primer specifically binds and the region of the pirA gene where the sixth oligonucleotide primer specifically binds, wherein the fourth oligonucleotide probe specifically binds a region of the pirB gene that is between the region of the pirB gene where the seventh oligonucleotide primer specifically binds and the region of the pirB gene where the eighth oligonucleotide primer specifically binds, and wherein the third and the fourth oligonucleotide probes are each coupled to a fluorophore and a quencher molecule. The fluorophore of the third oligonucleotide probe can be different from the fluorophore of the first, the second, and the fourth oligonucleotide probe and wherein the fluorophore of the fourth oligonucleotide probe is different from the fluorophore of the first, the second, and the third oligonucleotide probe.

The kit can include a fifth oligonucleotide probe adapted for real-time PCR amplification and detection, wherein the fifth oligonucleotide probe specifically binds a region of the 16S rRNA gene of *V. parahaemolyticus* that is between the region of the 16S rRNA gene of *V. parahaemolyticus* where the ninth oligonucleotide primer specifically binds and the region of the 16S rRNA gene of *V. parahaemolyticus* where the tenth oligonucleotide primer specifically binds, and wherein the fifth oligonucleotide probe is coupled to a fluorophore and a quencher molecule. The fluorophore of the fifth oligonucleotide probe is different from the fluorophore of the first, the second, third, and the fourth oligonucleotide probe The first oligonucleotide primer can have a sequence according to any one of SEQ ID NOs: 1 or 3. The second oligonucleotide primer can have a sequence according to any one of SEQ ID NOs: 2 or 4. The third oligonucleotide primer can have sequence according to SEQ ID NO: 14. The fourth oligonucleotide primer can have sequence according to SEQ ID NO: 15. The fifth oligonucleotide primer can have a sequence according to SEQ ID NO: 8. The sixth oligonucleotide primer can have a sequence according to SEQ ID NO: 9. The seventh oligonucleotide primer can have a sequence according to SEQ ID NO: 10. The eighth oligonucleotide primer can have a sequence according to SEQ ID NO: 11. The ninth oligonucleotide primer can have a sequence according to SEQ ID NO: 12. The tenth oligonucleotide primer can have a sequence according to SEQ ID NO: 13.

The kit can further include an amount of a detectable dye molecule that binds double stranded DNA. The detectable dye molecule that binds double stranded DNA is a cyanine dye. The detectable dye molecule that binds double stranded DNA is N',N'-dimethyl-N-[4-[(E)-(3-methyl-1,3-benzothiazol-2-ylidene)methyl]-1-phenylquinolin-1-ium-2-yl]-N-propylpropane-1,3-diamine and variants thereof.

In some embodiments a kit for detecting *Vibrio parahaemolyticus* (*V. parahaemolyticus*) in shrimp can include a first primer pair adapted for PCR, wherein the first primer pair comprises a first oligonucleotide primer and a second oligonucleotide primer; and/or a second primer pair adapted for PCR, wherein the second primer pair comprises a third oligonucleotide primer and a fourth oligonucleotide primer, wherein the first oligonucleotide primer is a forward direction oligonucleotide primer adapted for PCR amplification of a fragment of the pirA gene of *V. parahaemolyticus* with the second oligonucleotide primer and specifically binds a region of the pirA gene of *V. parahaemolyticus*, wherein the second oligonucleotide primer is a reverse direction oligonucleotide primer adapted for PCR amplification of a fragment of the pirA gene of *V. parahaemolyticus* with the first oligonucleotide primer and specifically binds a region of the pirA gene of *V. parahaemolyticus*, wherein the third oligonucleotide primer is a forward direction oligonucleotide primer adapted for PCR amplification of a fragment of the pirB gene of *V. parahaemolyticus* with the fourth oligonucleotide primer and specifically binds a region of the pirB gene of *V. parahaemolyticus*, and wherein the fourth oligonucleotide primer is a reverse direction oligonucleotide primer adapted for PCR amplification of a fragment of the pirB gene of *V. parahaemolyticus* with the third oligonucleotide primer and specifically binds a region of the pirB gene of *V. parahaemolyticus*.

The kit can further include a third primer pair adapted for PCR, wherein the third primer pair comprises a fifth oligonucleotide primer and a sixth oligonucleotide primer, wherein the fifth oligonucleotide primer is a forward direction oligonucleotide primer adapted for PCR amplification of a fragment of the 16S rRNA gene of *V. parahaemolyticus* with the sixth oligonucleotide primer and specifically binds a region of the 16S rRNA gene of *V. parahaemolyticus*, and wherein the sixth oligonucleotide primer is a reverse direction oligonucleotide primer adapted for PCR amplification of a fragment of the 16S rRNA gene of *V. parahaemolyticus* with the fifth oligonucleotide primer and specifically binds a region of the 16S rRNA gene of *V. parahaemolyticus*.

The kit can further include a fourth primer pair adapted for PCR, wherein the fourth primer pair comprises a seventh oligonucleotide primer and an eighth oligonucleotide primer, wherein the seventh oligonucleotide primer is a forward direction oligonucleotide primer adapted for PCR amplification of a fragment of a shrimp housekeeping gene (e.g. the 18S rRNA gene of shrimp) with the eighth oligonucleotide primer and specifically binds a region of the e.g. the 18S rRNA gene of shrimp), and wherein the eighth oligonucleotide primer is a reverse direction oligonucleotide primer adapted for PCR amplification of a fragment of e.g. the 18S rRNA gene of shrimp) with the seventh oligonucleotide primer and specifically binds a region of e.g. the 18S rRNA gene of shrimp).

The kit can further include a first oligonucleotide probe and/or second oligonucleotide probe, wherein the first oligonucleotide probe specifically binds a region of the pirA gene of *V. parahaemolyticus* that is between the region of the pirA gene of *V. parahaemolyticus* where the first oligonucleotide primer specifically binds and the region of pirB gene of *V. parahaemolyticus* where the second oligonucleotide primer specifically binds, wherein the first oligonucleotide probe is coupled to a fluorophore and a quencher molecule, and wherein the second oligonucleotide probe specifically binds a region of the pirB gene of *V. parahaemolyticus* that is between the region of the pirB gene of *V. parahaemolyticus* where the third oligonucleotide primer specifically binds and the region of pirB gene of *V. parahaemolyticus* where the fourth oligonucleotide primer specifically binds, wherein the second oligonucleotide probe is coupled to a fluorophore and a quencher molecule. The fluorophore of the first oligonucleotide probe can be different from the fluorophore of the second oligonucleotide probe.

The kit can further include a third oligonucleotide probe adapted for real-time PCR amplification and detection, wherein the third oligonucleotide probe specifically binds a region of the 16S rRNA gene of *V. parahaemolyticus* that is between the region of the 16S rRNA gene of *V. parahaemolyticus* where the fifth oligonucleotide primer specifically binds and the region of the 16S rRNA gene of *V. parahaemolyticus* where the sixth oligonucleotide primer specifically binds, wherein the third oligonucleotide probe is coupled to a fluorophore and a quencher molecule. The fluorophore of the third oligonucleotide probe can be different from the fluorophore of the first and the second, and the fourth oligonucleotide probe.

The kit can further include a fourth oligonucleotide probe adapted for real-time PCR amplification and detection, wherein the fourth oligonucleotide probe specifically binds a region of the beta actin gene or 18S rRNA gene of shrimp that is between the region of the beta actin gene or 18S rRNA gene of shrimp where the seventh oligonucleotide primer specifically binds and the region of the beta actin gene or 18S rRNA gene of shrimp where the eighth oligonucleotide primer specifically binds, and wherein the fourth oligonucleotide probe is coupled to a fluorophore and a quencher molecule. The fluorophore of the fourth oligonucleotide probe can be different from the fluorophore of the first, the second, and the third oligonucleotide probes.

The first oligonucleotide primer can have a sequence according to SEQ ID NO: 8. The second oligonucleotide primer can have a sequence according to SEQ ID NO: 9. The third oligonucleotide primer can have a sequence according to SEQ ID NO: 10. The fourth oligonucleotide primer can have a sequence according to SEQ ID NO: 11. The fifth oligonucleotide primer can have a sequence according to SEQ ID NO: 12. The sixth oligonucleotide primer can have a sequence according to SEQ ID NO: 13. The seventh oligonucleotide primer can have a sequence according to any one of SEQ ID NO: 14. The eighth oligonucleotide primer can have a sequence according to any one of SEQ ID NO: 15.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

*Necrotising hepatopancreatitis* (NHP) is a bacterial disease of penaeid shrimp caused by a Gram negative, intracellular pleomorphic alpha proteobacteria initially called NHPB and it just recently classified as *Hepatobacter penaei* (Nunan et al. 2013, that belongs to the order Rickettsiales in the new family Holosporales (Leyva et al. 2018). NHP affects cultured penaeid shrimp in several countries from the Americas including the United States of America, Mexico, Belize, El Salvador, Guatemala, Honduras, Costa Rica, Nicaragua, Panama, Brazil, Colombia, Ecuador, Peru and Venezuela (OIE 2017b, Lightner, 1996, Briñez et al. 2003; Aranguren et al. 2006). It has also been reported from an African country, Eritrea (Aranguren et al. 2010). NHP is a chronic disease that causes mortalities up to 50-95% in affected post-larvae (PL) (Loy & Harris 2008), juveniles (Lightner, 1996; Johnson, 1989) and broodstock of *Penaeus vannamei* (Aranguren et al. 2006. Morales et al. 2006). The manifestation of NHP at farming level is related to particular environmental conditions such as high salinity and high temperature (Lightner 1996; Vincent & Lotz, 2007). NHP-infected shrimp show a typical soft shell, flaccid bodies, reduced feed intake and empty midguts (Lightner 1996). The acute phase lesions in diseased shrimp include necrosis and sloughing off of epithelial cells in hepatopancreas (HP) tubule, intracellular hemocytic response, and melanized HP tubules. In chronic phase, the HP lesions are characterized by atrophy of tubules, reduced epithelial cell height, low lipid storage R cells and intratubular edema (Lightner 1996). Since the first report in 1985 (Frelier et al. 1993), NHP has become such an important disease in the shrimp industry that on 2010 it was listed in the OIE-list of crustacean diseases (OIE 2017a).

Several diagnostic methods have been developed to detect and confirm *H. penaei* presence including PCR, histology and in-situ hybridization (Lightner 1996; Loy & Frelier 1996; Nunan et al. 2008; Aranguren et al. 2010) and qPCR (Vincent & Lotz 2005; Aranguren et al. 2010), however, there is only one PCR method recommended in the OIE manual (OIE 2017b) and that creates the need to have an alternative PCR and real-time PCR (qPCR) assays for *H. penaei* detection and confirmation, especially when new non-specific amplifications are being observed while screening *Artemia* cysts for *H. penaei* (FIG. 1).

Bacterial flagella are complex and well-honed organelles that provide swimming and swarming motilities and play a central role in adhesion, biofilm formation, and host invasion (Kirov 2003). The typical bacterial flagellum consists of six components: a basal body (including MS ring, P ring, and L ring), a motor, a switch, a hook, a filament, and an export apparatus (McNab 2003). The core set of flagellar genes, that is uniformly present in all flagellated bacteria, has evolved and diverged in a lineage-specific manner (Liu & Ochman 2007). This makes flagellar genes highly specific for a specific bacterial group. We describe here PCR-based detection methods targeting flagellar genes that are specific for *H. penaei* and do not provide non-specific amplification in *Artemia* samples.

This Example discusses, inter alia, a PCR and real-time method for *H. penaei* detection with high sensitivity and higher specificity in comparison with the current OIE method. In addition, the cause of non-specific amplification while screening samples for *H. penaei* based on 16S rRNA gene was investigated. Lastly, possible Glades among *H. penaei* isolates through a phylogenetic analysis was examined. Considering the diversity that exists among geographical isolates of *H. penaei*, and the need to develop an alternative method to avoid non-specific amplification, the detection methods described here are major improvements in *H. penaei* screening.

Materials and Methods

The *H. penaei* positive samples used in this study originated in USA Texas (samples a & b from 2016), Ecuador (2011) Mexico (2013), Texas, USA (samples a, b & c from 2013), Ecuador (samples a & b from 2015) and Honduras (2016). Those samples have been archived at The University of Arizona Aquaculture Pathology laboratory (UAZ-APL)

HP samples were preserved in 95% ethanol. *Artemia* cysts were sampled from either an *Artemia* cyst can (454 g size) or a plastic container. From each can/container, 25 g were sub-sampled from the top, one from the middle and one from the bottom of the can. Three sub-samples were then mixed and approx. 25 mg taken for the isolation of DNA.

DNA Extraction

DNA extraction was carried out from hepatopancreas (HP) and *Artemia* cysts. Approximately 25-50 mg of HP tissue/*Artemia* cysts was taken for DNA extraction using a Maxwell® 16 Cell LEV DNA Purification Kit and following the manufacturer's protocol. Upon extraction the DNA was stored at −20° C. until further analysis.

PCR

The nucleotide sequence of the flagellar hook protein gene flgE of *H. penaei* (GenBank JQAJ01000001.1) (Wang & Wu 2014) that encodes for the hook subunit of the flagellum was used to design *H. penaei* primers using Primer Express 3.0 (Applied Biosystems). PuReTaq Ready-To-Go PCR beads were used for the PCR assay. The primers for detecting the *H. penaei* were NHP FlgE1143F: 5'-AGG-CAA-ACA-AAC-AAC-CCT-TG-3' (SEQ ID NO: 1) and the NHP flgE1475R: 5'-GCG-TTG-TTG-TTG-GGA-AAG-TT-3'. (SEQ ID NO: 2) Amplifications were performed with the following cycling parameters: initial denaturation at 95° C. for 5 min, followed by 35 cycles of 95° C. for 30 s, 62° C. for 30 s, and 72° C. for 30 s, and a final extension at 72° C. for 5 min to generate an amplicon of 333 bp from the NHP flgE gene region.

To test the sensitivity of NHP FlgE-primers, PCR assays were performed using DNA from 10 NHP positive samples following the new assay vs. the conventional PCR protocol recommended by OIE (Aranguren et al. 2010).

To test the specificity of NHP FlgE-primers, PCR assays were performed with DNA isolated from shrimp infected with five different bacterial pathogens: *H. penaei*, *Vibrio parahaemolyticus*, *V. harveyi*, *Spiroplasma penaei* and *V. parahaemolyticus* causing AHPND/EMS. In addition, DNA isolated from shrimp infected with viruses, IMNV, YHV-genotype 1, IHHNV, WSSV, TSV were tested. DNA isolated from specific-pathogen-free (SPF) *Penaeus vannamei* was taken as negative control for the PCR assay. In addition, samples of *Artemia* cysts that displayed non-specific amplification using the OIE method were run with the NHP FlgE primers. The unusual bands were purified from the electrophoresis gel using the QIAquick PCR purification kit (Qiagen) and sent for sequencing in both directions.

Quantitative PCR (qPCR)

The primers and the TaqMan hydrolysis probe were designed using "Primer Express software version 3.0" (Applied Biosystems) from the flagella hook gene flgE. of *H. penaei*. Primers (NHP FlgE3qF: 5'-AAC-ACC-CTG-TCT-CCC-CAA-TTC-3' (SEQ ID NO: 3) and NHP FlgE3qR: 5'-CCA-GCC-TTG-GAC-AAA-CAC-CTT-3') (SEQ ID NO: 4) were used to produce a PCR product of 63 base pair (bp). The TaqMan probe NHP: 5'-CGC-CCC-AAA-GCA-TGC-CGC-3', (SEQ ID NO: 5) was synthesized and labeled with fluorescent dyes 6-carboxyfluorescein (FAM) on the 5' and N,N,N,N-tetramethyl-6-carboxyrhodamine (TAMRA) on the 3' end. The amplification reactions were conducted as follow: 0.5 µM of each primer, 0.1 µM of TaqMan probe, 1× TaqMan Fast virus 1-step Master Mix (Life Technologies), 5-50 ng of DNA and HPLC water in a reaction volume of 10

µl. The qPCR profile consisted of 20 sec at 95° C. followed by 40 cycles of 1 s at 95° C. and 20 sec at 60° C. Amplification detection and data analysis for qPCR assays were carried out with StepOnePlus real-time PCR system (Life Technologies).

Generating a Standard Curve for Quantification of *H. penaei*

To generate a plasmid DNA standard for the NHP flgE qPCR assay, the primers NHP flgE 1143F and 1475R were used to amplify a 333-bp product from the NHP FlgE gene. The PCR product was cleaned using a QIAquick PCR purification kit (Qiagen). The amplicon was cloned into a pCR2.1-TOPO TA vector (Invitrogen) and transformed into *Escherichia coli* JM109 cells (Promega). The recombinant plasmid pNHPFlgE was verified by DNA sequencing in both orientations with an automated Applied Biosystems 3730 DNA Analyzer. The concentration of pNHPFlgE was determined by measuring the optical density at 260 nm in a Nanodrop™. The optical density of each sample was measured five times and the average OD result was used to estimate the amount of DNA present in the sample. The quality of DNA was checked using the 260:280 ratio. The DNA copy number was obtained by using the formula: (Amount of DNA in ng) (Avogadro's number)/(650 Da) (length of template as bp) (Staroscik, 2004). The analytical sensitivity of the qPCR was determined using 10-fold dilutions of purified plasmid pNHPFlgE. The plasmid DNA was diluted using a carrier, DNA from a SPF shrimp *Penaeus vannamei* at a concentration of 10 ng/µl. The concentration of plasmid DNA used to generate a standard curve from $10^8$ to 1 copy per reaction. The assay was repeated six times to determine the reproducibility.

Phylogenetic Analysis

Oligonucleotide primers NHP16S rRNA F2: 5'-GTG-GCA-GAC-GGG-TGA-GTA-AT-3' (SEQ ID NO: 6) and NHP16S rRNAR2: 5'-CCT-CCA-TTG-CTG-GTT-AGC-TC-3', (SEQ ID NO: 7) which generated a 1321-bp amplicon, were used in the end-point PCR analysis. The NHP16S rRNA corresponds to GenBank Accession number U65509.1. The primer concentration (F2/R2) used for each was 0.2 µM. PCR was conducted in a final volume of 25 µL. PuRetaq ready-to-Go PCR beads (GE Healthcare) were used. The cycling parameters were as follows: 1 cycle at 95° C. followed by 35 cycles of 95° C. for 30 s, 58° C. for 45 s, and 72° C. for 45 s, and a final extension at 72° C. for 5 min. All amplifications were performed in a Veriti 96-well thermal cycler (Applied Biosytems). Following amplifications, the PCR products were electrophoresed in 1.5% agarose gels containing 0.5 µg ml$^{-1}$ ethidium bromide and visualized under ultraviolet light and digitally photographed by the Alphalmager (Alpha Innotech). PCR product was purified using the QIAquick PCR Purification Kit (QIA-GEN) and sent for sequencing in both directions. Assembly of the sequence was carried out by overlapping amplified regions using Geneious 4.8.5 software, with NHP 16S rRNA (Accesion number U65509.1) (Loy et al. 1996) as a template. Multiple sequence alignment and phylogenetic analyses were performed with Clustal X (Thompson et al. 1997). The phylogenetic tree was inferred by using the Maximum Likelihood method based on the Tamura-Nei model Tamura & Nei 1993). The bootstrap consensus tree inferred from 1000 replicates (Felsenstein 1995). The analysis involved 12 nucleotide sequences. All positions containing gaps and missing data were eliminated. There was a total of 1131 positions in the final dataset. Evolutionary analyses were conducted in MEGA7 (Kumar et al. 2016). Evolutionary Divergence between Sequences was conducted using the Maximum Composite Likelihood model.

Results

Non-Specific Amplification

The PCR electrophoresis gel from two samples of *Artemia* cysts displayed some non-specific bands using the 16S rRNA primers (left side) with an amplicon of about 400 bp (FIG. 1). In contrast, on the right side of FIG. 1 is shown the same sample set amplified with the FlgE primers. Unlike the amplification using the 16S rRNA primers, with the FlgE primers there are no amplification products in the electrophoresis gel. The sequencing data revealed that the amplicon obtained using the 16S rRNA primers did not correspond to *H. penaei*, and that confirmed the non-specific amplification in samples of *Artemia* cysts. The nature of the non-specific product in *Artemia* samples was further analyzed by comparing the amplicon sequence with the NCBI database. BLASTN analysis revealed that the sequence of the sample coded 689 has highest similarity to a bacterium *Halanaerobium* sp (98% identity) (GenBank seq FJ858788.1). The best alignment of the sequence of the sample 316 was with an uncultured bacterium (96% identity) (GenBank seq: JX882300.1).

Analytical Sensitivity and Specificity z of qPCR

Figure 2:
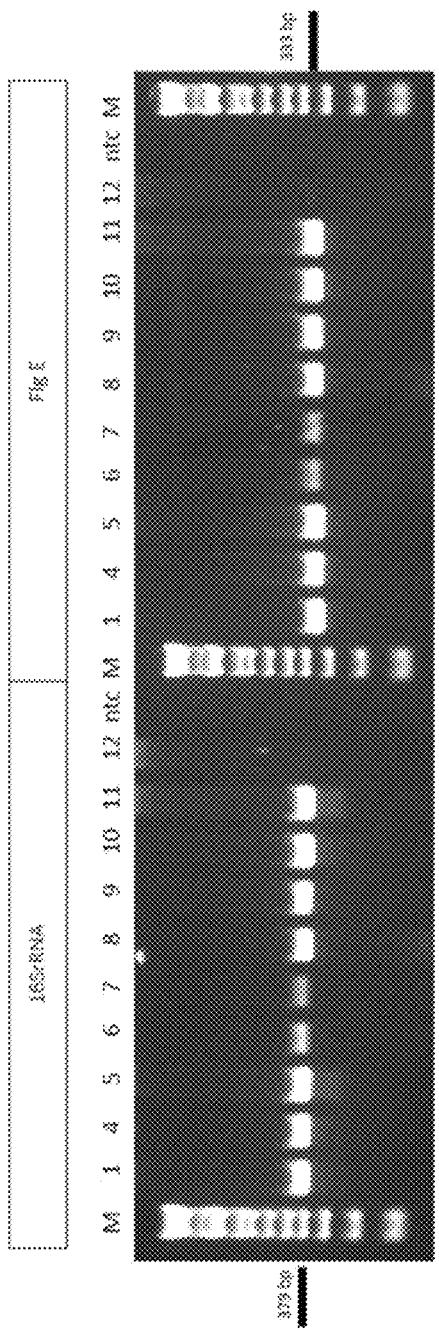
FIG. 2 shows PCR detection of *Hepatobacter penaei* (*H. penaei*) in twelve different samples of infected *Penaeus vannamei* hepatopancreas based on 16S rRNA and flgE genes. M: 1 kb plus ladder molecular weight marker; ntc, Non template control; 1, Ecuador 2015; 4, Mexico 2013; 5, Texas 2013; 6, Belize 2016; 7, Panama 2016; 8, Texas 2006a; 9, Honduras 2016; 10, Texas 2006b; 11, Texas 2013b; 12; Brazil 2012).

The analytical sensitivity of the NHP PCR was determined by using *H. penaei* in 10 different independent samples from 7 origins with two different set of primers: 16S rRNA and Flg E (FIG. 2). In FIG. 2 the left side of the gel shows samples amplified by using the current OIE-recommended method (16S rRNA); on the right side, the same samples amplified by the new method. Both methods provided similar results, and similar intensity in the gel bands. Samples 12 (Brazil 2012) show very weak amplification in both protocols, which suggest partial DNA degradation. Despite this, the conventional PCR method based on flgE gene is comparable to 16S rRNA based PCR.

Figure 3:
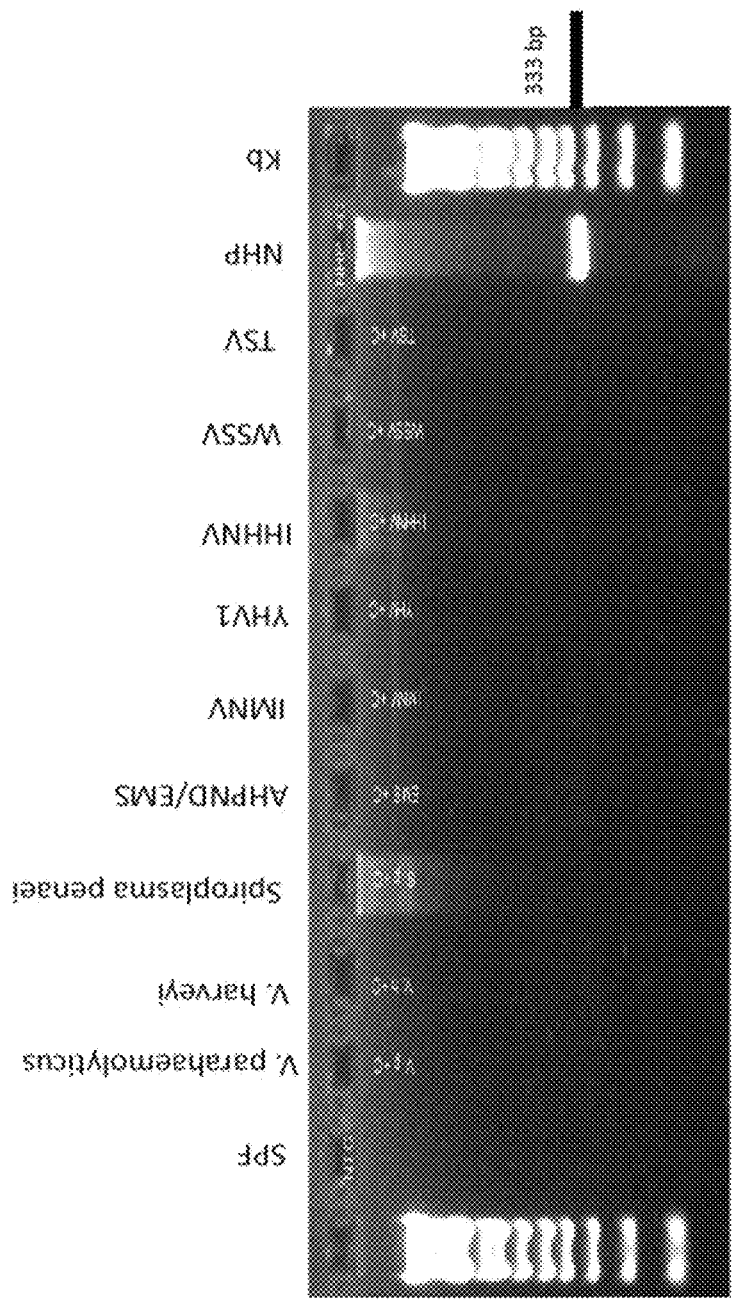
FIG. 3 shows PCR detection of *Hepatobacter penaei* (*H. penaei*) in positive controls of shrimp pathogens including *V. parahaemolyticus*, *V. harveyi*, *Spiroplasma penaei*, AHPND causing *V. parahaemolyticus*, IMNV, IHHNV, WSSV, TSV and *H. penaei* (NHP). A SPF sample was included as a negative control in the assay.

In order to determine specificity of amplification using the flgE protocol, DNA extracted from shrimp infected with viral diseases, including IMN, YHD, IHHN, WSD and TS and, bacterial diseases including *V. parahaemolyticus*, *V. harveyi*, *Spiroplasma penaei*, *V. parahaemolyticus* causing AHPND and *H. penaei* were used as templates for PCR amplification. Negative results were obtained for all shrimp diseases except *H. penaei*. (FIG. 3). This indicates the specificity of the primers for the flgE gene albeit a narrow range of Gram negative bacteria that are known to affect shrimp.

Analytical Sensitivity of Quantitative PCR (qPCR)

Figure 4:
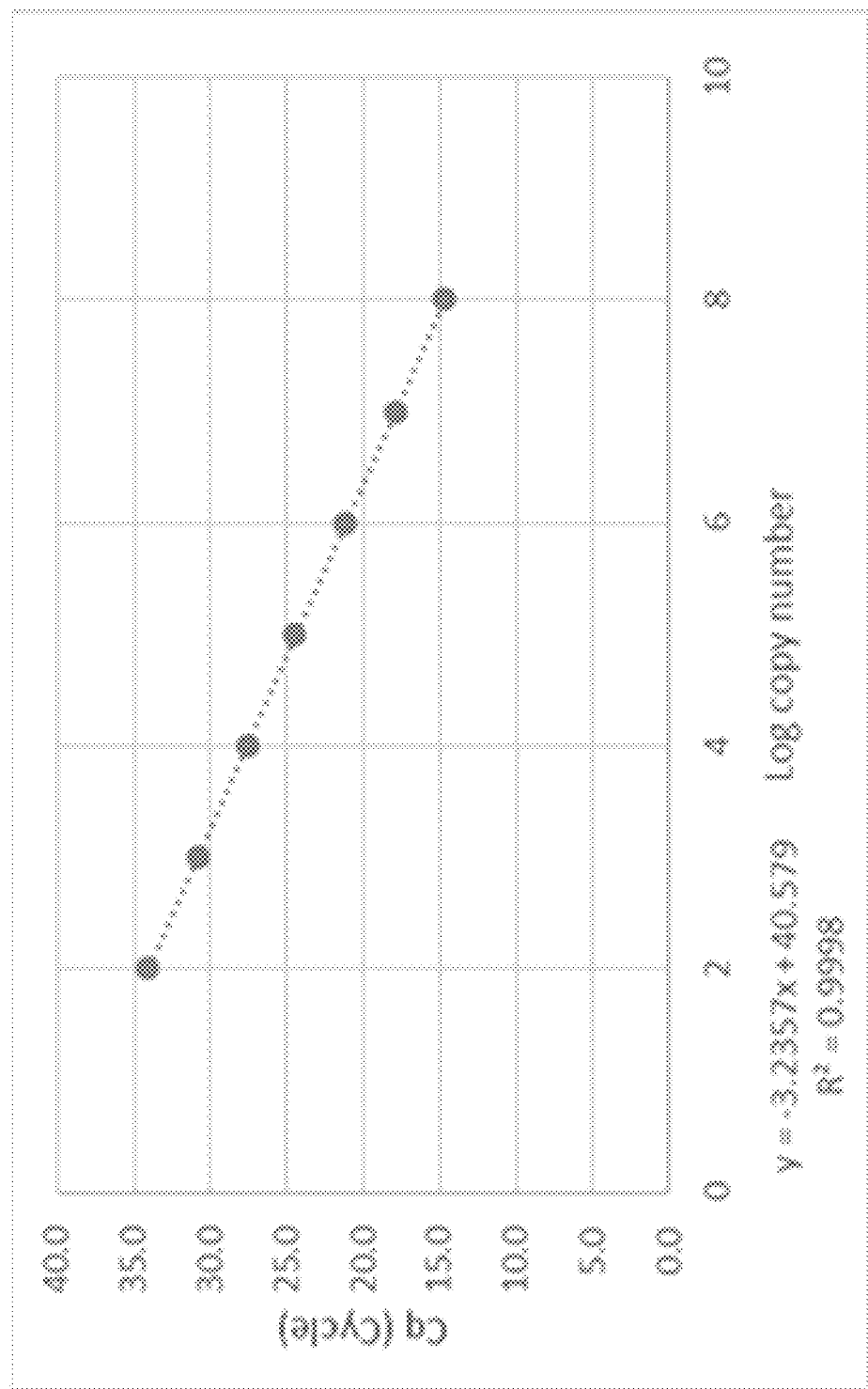
FIG. 4 shows a graph that can demonstrate a Standard curve of the *H. penaei* copy number versus Cq (Quantification cycle) value. Purified pNHPFlgE plasmid was serially diluted from $1\times10^8$ to 100 copies and used as template in qPCR.

In order to determine the analytical sensitivity of the NHP FlgE qPCR protocol, a 333-bp *H. penaei* fragment of the flgE gene having the target sequence was used as a standard. A ten-fold dilution series of the plasmid was tested using $1\times10^1$ to $1\times10^8$ copies. *H. penaei* was detected at 100 copies *H. penaei* in all six assays within a 0.0-0.2 standard deviation (SD) (Table 1). Therefore, the detection limit was 100 copies (FIG. 4). To establish the reproducibility of the *H. penaei* qPCR, six standard curves were compared in a 7-log range from $1\times10^2$ to $1\times10^8$ copies per reaction (Table 1).

The SD within each run ranged from 0.0 to 0.5 in $10^2$ copies and from 0.0 to 0.5 in the $10^8$ copies. In the combined data from six independent runs, there was no linear relationship between the quantification cycle (Cq) values (also called threshold cycle, Ct) and the SD (p>0.05). For the inter-assay replicates, the SD values between 0.3 and 0.9 were found, indicating good reliability in this assay (Table 1). The correlation coefficient ($R^2$) of these six standard curves were always greater than 0.99, indicating good reproducibility, and the reaction efficiency values fluctuated between 0.99 through to 1.08. The mean slope was -3.23 and the intercept 40.58 indicating a high efficiency of the PCR, hence good optimization of the protocol (FIG. 4).

Comparison of 16S rRNA NHP vs. flgE qPCR

Figure 5:
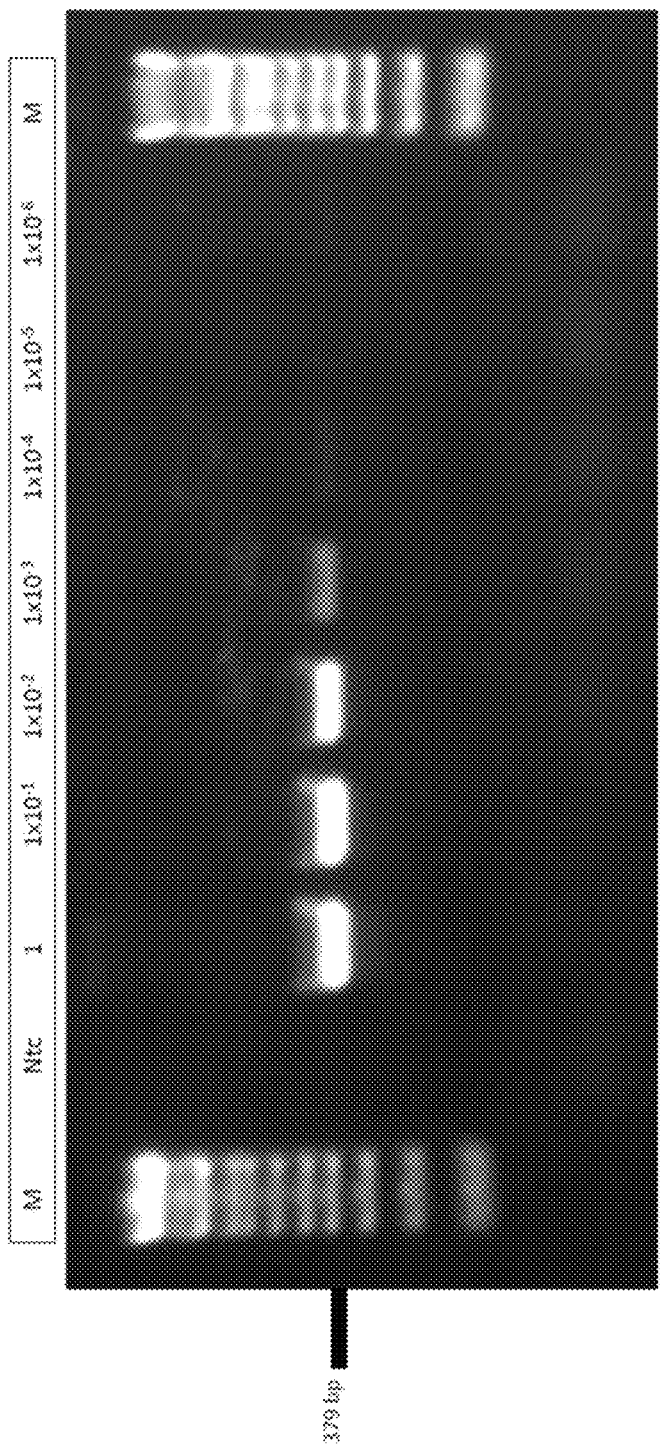
FIG. 5 shows *H. penaei* amplification using conventional PCR based on NHP 16S rRNA gene and using six serially diluted samples of template DNA. Samples 1 contain $2.06\times 10^6$ NHP copies $\mu l^{-1}$ of DNA. Ntc: no template control, M: 100 bp ladder.
Figure 6:
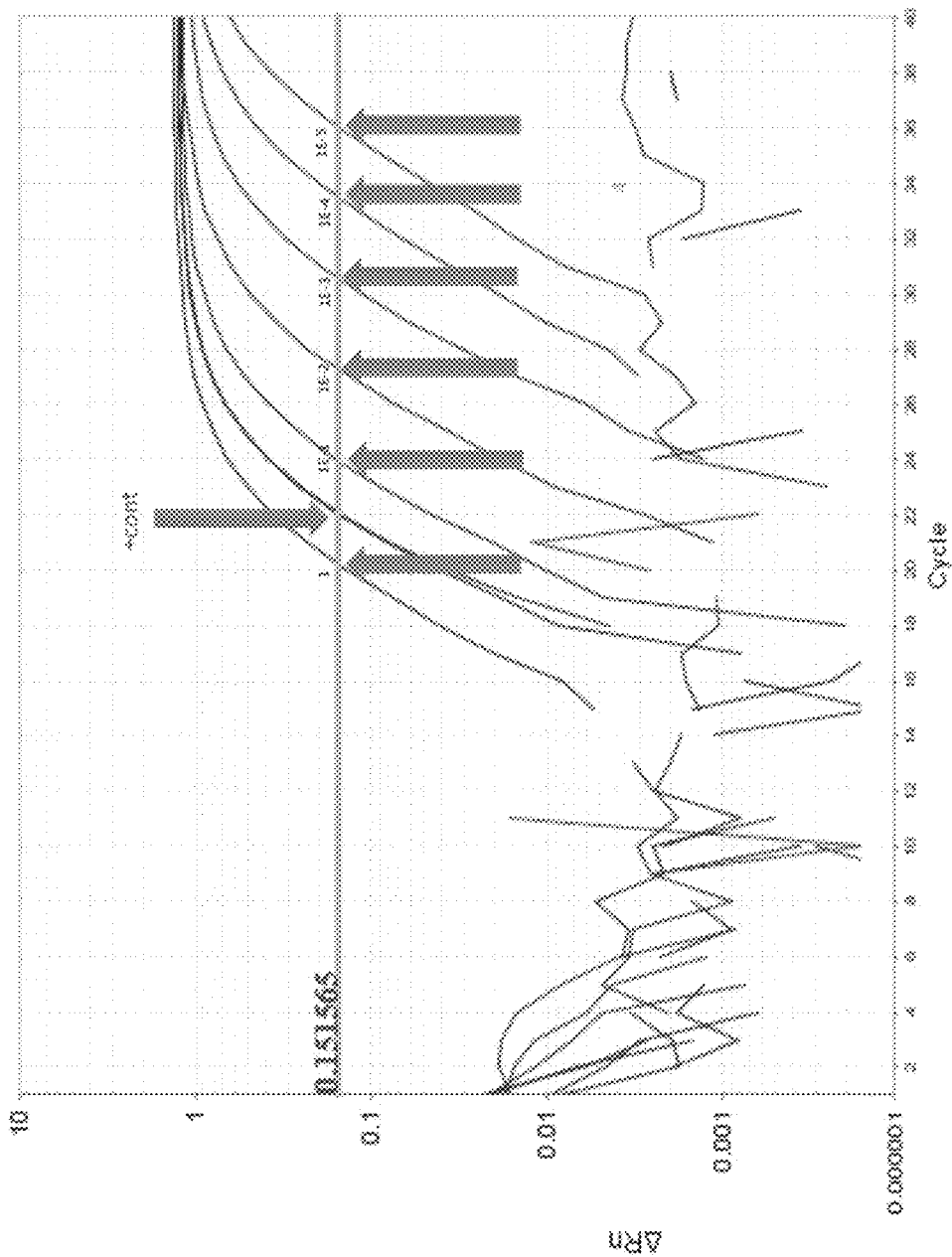
FIG. 6 shows a graph that can demonstrate Ct curves showing H. penaei amplification using real-time PCR based on the NHP flgE gene and using six serially diluted template DNA. Samples 1 contained 2.06×10$^6$ NHP copies µl$^{-1}$ of DNA.

To determine the difference in sensitivity between the new FlgEqNHP assay vs. the current OIE-recommended end point PCR method, a positive sample with a known copy number ($2.06 \times 10^6$ H. penaei copies $\mu l^{-1}$ of DNA) was use in serial dilutions from $10^6$ through to $10^1$. This series of samples were run by both PCR and qPCR. By using qPCR, samples diluted up to $1 \times 10^{-5}$ ($2.06 \times 10^1$ copies $\mu l^{-1}$ of DNA) were detected by this qPCR (FIG. 6). The same samples run by the end-point PCR could detect down to $2.06 \times 10^3$ copies reliably, and sample containing $2.06 \times 10^2$ copies provided a faint band (a weak positive result) (FIG. 5). Samples with a lower bacterial concentration ($2.06 \times 10^1$ copies $\mu l^{-1}$ of DNA) and lower were not detected with the H. penaei PCR assay.

Phylogenetic Analysis of the NHP 16S rRNA Sequence

Figure 7:
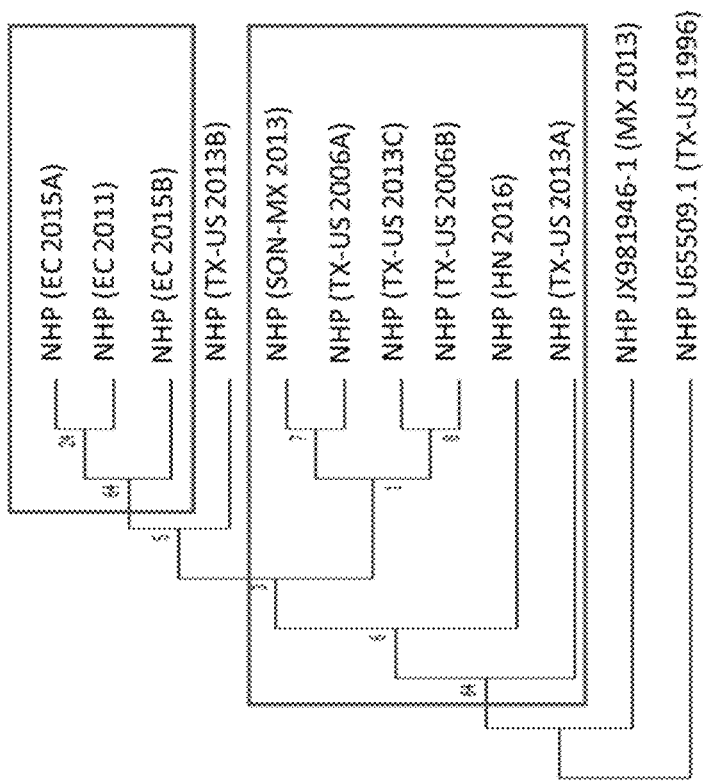
FIG. 7 shows a Maximum Likelihood phylogenetic tree based on the Tamura-Nei model from the alignment of the 16S rRNA sequences among twelve H. penaei (NHP) geographical isolates. Numbers indicate the bootstrap support from 1000 replicates. Bootstrap values (>50%) are indicated next to the branches.
Figure 8:
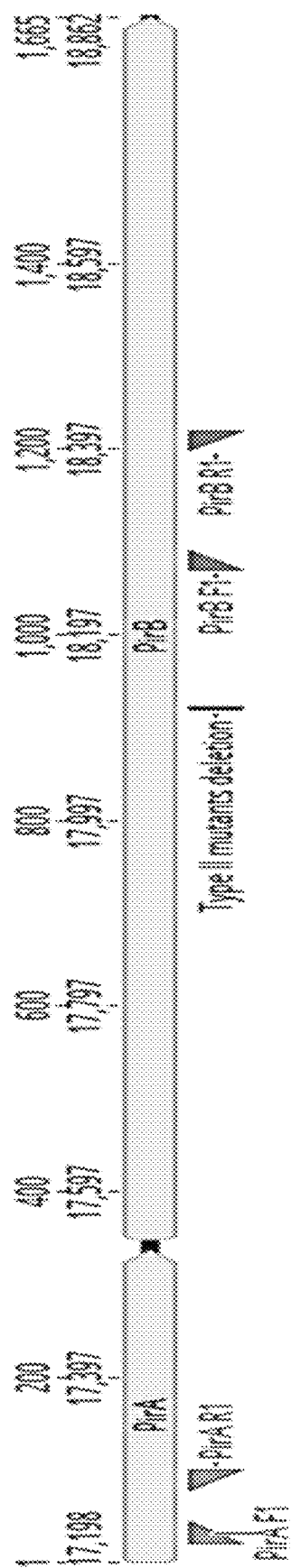
FIG. 8 shows the PirA and PirB primer locations on the virulence plasmid from reference strain A3. The primers PirA F1, PirA R1, PirB F1 and PirB R1 for dual detection of PirA and PirB are shown in green. The PirB primer are located in the second half of the PirB gene allowing the detection of type II mutants. The section up to where the deletion of the PirA and PirB genes occurs is shown in red (type II deletion mutants II).

A phylogenetic tree was constructed based on the nucleotide sequences of 1.131 kb amplicon of 16S rRNA obtained for twelve H. penaei isolates (FIG. 7). The NHP sequences clustered into two clear groups. In one clade, samples from Ecuador (EC 2011, GenBank Accession number: MH230903) and EC2015a (MH230902), EC2015b (MH230909) grouped together with a bootstrap value of 64%. On the other hand, samples from Mexico 2013 (MH230904), Honduras 2016 (MH 230907) and the USA TX-US 2006a (MH230906), USA TX-US 2006b (MH230900), USA TX-US 2013a (MH230908), USA TX-US 2013c (MH230905) clustered together with a bootstrap value of 64% as well. One sample from USA TX-US 2013b (MH230901) did not group with the NHP TX samples. DNA sequence of NHP from 1996 that was used as the root sequence, differed from the new NHP sequences from 2006-2016 (FIG. 6). The number of base substitutions per site from between sequences are shown in Table 2. The nucleotide identity among the NHP 16S rRNA sequences ranged between 99.64 and 100.00%.

Discussion

In order to minimize the introduction of shrimp pathogens in shrimp-producing countries a series of biosecurity strategies have been developed including testing shrimp and shrimp-related products for the OIE listed pathogens that affect shrimp. The variety of samples have been challenging for the PCR diagnosis lab in terms of presence of unexpected results including the report here of non-specific bands recently observed in *Artemia* cysts.

This Example discusses, inter alia, PCR and qPCR assays were developed to detect and quantify H. penaei in shrimp tissues using the NHP flgE gene. This new-end point PCR assay has a similar sensitivity to the currently recommended OIE H. penaei assay. However, the specificity of the new PCR assay is higher, and non-specific positive results obtained with samples tested using 16S rRNA gene were not seen with this new H. penaei flgE PCR assay. This could be explained by the fact that the target gene, flgE for the PCR is highly bacterium-specific compared to 16S rRNA gene. As a result, PCR based on flgE gene is unlikely to provide false positive results in a variety of samples, including *Artemia* cysts and shrimp tissues, analyzed by the UAZ-APL.

The non-specific amplification of *Artemia* samples using the OIE H. penaei assay is due to the possible presence of uncultured bacteria living in hypersaline conditions with a similar H. penaei 16S rRNA sequence. *Artemia* cysts are naturally present in hypersaline environments (FAO 2011); hence, it is likely that during its harvesting process, some bacteria remained attached to or inside the harvested cysts. Considering the fact that field collected shrimp samples and shrimp-related samples often carry more than one pathogen, the specificity of the newly developed methods will enable us to avoid non-specific amplifications. In addition, when evaluating the specificity with other shrimp pathogens, the only positive result was found with the H. penaei isolate indicating the high specificity of this assay.

The qPCR assay discussed in this Example showed a detection limit of $1 \times 10^2$ copies. Comparison between the OIE qPCR method versus this new qPCR assay are consistent and Cq values are similar (data not shown). The sensitivity of this qPCR method based on flgE is similar to the OIE qPCR method based on the 16srRNA. The method described herein is more specific than the OIE method.

In addition, samples from 4 different geographical areas including Mexico, USA, Honduras and Ecuador collected in different years allowed confirmation of the specificity of this new qPCR. So far there are only two previous studies that reported H. penaei quantification in shrimp tissue (Vincent & Lotz, 2005; Aranguren et al. 2010). While attempting to reproduce the results reported by Vincent and Lotz (2005), inconsistent results in the H. penaei copy number were obtained (Aranguren et al. 2010). Later, a more reproducible method was developed by the UAZ-APL (Aranguren et al. 2010). However, the fact that the target region is based on the 16S rRNA, some non-specific amplification may be expected. A qPCR method based on flgE gene will allow avoidance of this scenario.

The phylogenetic analysis based on the 16S rRNA gene showed two clusters, one cluster contained isolates from Ecuador, while the second cluster contained isolates from Mexico and Texas, USA. Samples from Ecuador in 2011 and 2015 were grouped in the same cluster which suggests the presence of the same H. penaei isolate. Another possibility is a low mutation rate of this H. penaei. In contrast, some samples from Mexico (2006 & 2013) and Texas, USA (2013) grouped together. These two geographical areas are close together, indicating that the same H. penaei isolate could be present in both countries due to the marine currents and/or movement of NHP-infected shrimp between the two geographically separated areas. The ability to detect H. penaei in a wide range of geographical isolates will be useful for routine screening of H. penaei, and to avoid false negatives.

NHP has been reported in sub-adults and broodstock populations in farms (Aranguren et al. 2006) and juvenile (Lightner 1996) population causing different mortality pattern (Briñez et al. 2003; Aranguren et al. 2010). In some countries such as in Colombia, NHP does not cause the acute mortalities as reported in other countries and the typical NHP clinical signs are not always detected (Aranguren et al. 2006). This phenomenon could be related to the resistance of some *P. vannamei* lines to NHP (Aranguren et al. 2010). It is also possible that H. penaei isolates may vary in their pathogenicity which could explain the different mortality pattern in different regions. The ability to detect down to 100 copies in the qPCR assay based on the flgE gene will be very useful in detecting H. penaei in samples that display subclinical sign or no sign at all.

In summary, this Example discusses, inter alia, a conventional PCR and a real-time PCR assays as alternative methods for the diagnosis and quantification of H. penaei in shrimp and shrimp-associated samples. The assay is highly specific and sensitive. The sensitivity of the flgE NHP PCR is similar to the currently recommended OIE method, but it is more specific and sensitive; hence it may be a better diagnostic tool for this pathogen.

REFERENCES

Aranguren L F, Tang K F, Lightner D V (2010) Quantification of the bacterial agent of necrotizing hepatopancreatitis (NHP-B) by real-time PCR and comparison of survival and NHP load of two shrimp populations. Aquaculture 307:187-192

Aranguren L F, Briñez B, Aragón L, Platz C, Caraballo X, Suarez A, Salazar M (2006) Necrotizing hepatopancreatitis (NHP) infected Penaeus vannamei female broodstock: Effect on reproductive parameters, nauplii and larvae quality. Aquaculture 258:337-343

Briñez B, Aranguren F, Salazar M (2003) Fecal samples as DNA source for the diagnosis of necrotizing hepatopancreatitis (NHP) in Penaeus vannamei broodstock. Dis Aquat Org 55:69-72

FAO 2011. Fisheries and Aquaculture Department online. Rome. Updated 11 Oct. 2011. http://www.fao.org/fishery/culturedspecies/Artemia_spp/en FAO 2016. Programa Regional para el Fortalecimiento de los Sistemas de Sanidad Animal y Vegetal Sanidad Animal (Pecuaria, Pesquera y Acuicola). TCP/RLA/3606.

Frelier P F, Loy J K, Kruppenbach B (1993) Transmission of necrotizing hepatopancreatitis in Penaeus vannamei. J Invertebr Pathol 61:44-48

Johnson S (1989) Handbook of shrimp diseases. Texas A&M Sea Grant College Program. Galveston, Tex. Publ. No. TAMU-SG-75-603: 1-23

Kirov S M (2003) Bacteria that express lateral flagella enable dissection of the multifunctional roles of flagella in pathogenesis. FEMS Microbiol Lett 224:151-159

Kuhner M K, Yamato J, Felsenstein J (1995) Estimating effective population size and mutation rate from sequence data using Metropolis-Hastings sampling. Genetics 140: 1421-1430

Kumar S, Stecher G, Tamura K (2016) MEGA7: molecular evolutionary genetics analysis version 7.0 for bigger datasets. Mol Biol Evol 33:1870-1874

Leyva J M, Martinez-Porchas Marcel, Hernandez-Lopez Jorge, Vargas-Albores Francisco, Gollas-Galván Teresa (2018) Identifying the causal agent of necrotizing hepatopancreatitis in shrimp: Multilocus sequence analysis approach. Aquacult Res 0, D01:10.1111/are.13633

Lightner D V (1996) A handbook of shrimp pathology and diagnostic procedures for diseases of cultured penaeid shrimp.

Liu R, Ochman H (2007) Stepwise formation of the bacterial flagellar system. Proc Natl Acad Sci USA 104:7116-7121, D01:0700266104 [pii]

Loy J K, Frelier P F, Varner P, Templeton J W (1996) Detection of the etiologic agent of necrotizing hepatopancreatitis in cultured Penaeus vannamei from Texas and Peru by polymerase chain reaction. Dis Aquat Org 25:117-122

Macnab R M (2003) How bacteria assemble flagella. Annual Reviews in Microbiology 57:77-100

Morales Covarrubias M, Osuna-Duarte A, Garcia-Gasca A, Lightner D, Mota-Urbina J (2006) Prevalence of necrotizing hepatopancreatitis in female broodstock of white shrimp Penaeus vannamei with unilateral eyestalk ablation and hormone injection. J Aquat Anim Health 18:19-25

Nunan L, Lightner D, Pantoja C, Gomez-Jimenez S (2014) Detection of acute hepatopancreatic necrosis disease (AHPND) in Mexico. Dis Aquat Org 111:81-86

Nunan L M, Pantoja C, Lightner D V (2008) Improvement of a PCR method for the detection of necrotizing hepatopancreatitis in shrimp. Dis Aquat Org 80:69-73

OIE. 2017a. Aquatic animal health code (2017). Paris, World Organisation for Animal Health. (available at: http://www.oie.int/international-standard-setting/aquatic-code/access-online/)

OIE. 2017b. Manual of diagnostics tests for aquatic animals (2017). Paris, World Organisation for Animal Health, (available at: http://www.oie.int/international-standard-setting/aquatic-manual/access-online/)

Staroscik A (2004) Calculator for determining the number of copies of a template. URI Genomics & Sequencing Center 19:2012

Tamura K, Nei M (1993) Estimation of the number of nucleotide substitutions in the control region of mitochondrial DNA in humans and chimpanzees. Mol Biol Evol 10:512-526, DOI:10.1093/oxfordjournals.molbev.a040023 [doi]

Thompson J D, Gibson T J, Plewniak F, Jeanmougin F, Higgins D G (1997) The CLUSTAL_X windows interface: flexible strategies for multiple sequence alignment aided by quality analysis tools. Nucleic Acids Res 25:4876-4882

Vincent A G, Lotz J M (2005) Time course of necrotizing hepatopancreatitis (NHP) in experimentally infected Litopenaeus vannamei and quantification of NHP-bacterium using real-time PCR. Dis Aquat Org 67:163-169

Vincent A G, Lotz J M (2007) Effect of salinity on transmission of necrotizing hepatopancreatitis bacterium (NHPB) to Kona stock Litopenaeus vannamei. Dis Aquat Org 75:265-268.

Tables

TABLE 1

Reproducibility of the TaqMan real time qPCR assay for detecting H. penaei in six different assays.

| NHP copies | Intra-assay SD (Average Cq value for duplicate) | | | | | | Inter-assay SD (Mean Cq value) |
|---|---|---|---|---|---|---|---|
| | 1 | 2 | 3 | 4 | 5 | 6 | |
| $1 \times 10^2$ | 0.5 (34.6) | 0.1 (34.9) | 0.0 (32.9) | 0.1 (34.1) | 0.5 (33.6) | 0.0 (35.4) | 0.90 (34.2) |
| $1 \times 10^3$ | 0.1 (31.1) | 0.2 (31.3) | 0.3 (30.0) | 0.7 (30.2) | 0.3 (30.9) | 0.1 (31.0) | 0.54 (30.8) |
| $1 \times 10^4$ | 0.1 (28.0) | 0.2 (28.0) | 0.1 (27.5) | 0.3 (26.5) | 0.5 (27.5) | 0.2 (27.8) | 0.57 (27.5) |
| $1 \times 10^5$ | 0.0 (24.7) | 0.2 (25.1) | 0.0 (24.4) | 0.5 (23.4) | 0.2 (25.1) | 0.1 (24.4) | 0.63 (24.5) |
| $1 \times 10^6$ | 0.1 (21.2) | 0.0 (22.0) | 0.0 (21.1) | 0.3 (20.8) | 0.2 (21.1) | 0.2 (21.1) | 0.43 (21.2) |
| $1 \times 10^7$ | 0.0 (18.0) | 0.5 (18.5) | 0.2 (17.8) | 0.2 (17.8) | 0.4 (17.6) | 0.1 (17.9) | 0.30 (17.9) |
| $1 \times 10^8$ | 0.0 (14.9) | 0.2 (15.2) | 0.0 (14.4) | 0.0 (14.4) | 0.5 (14.5) | 0.4 (14.6) | 0.32 (14.7) |

SD: Standard Deviation;
Cq: Quantification cycle

TABLE 2

Estimates of nucleotide similarity among geographical isolates of *H. penaei* based on the 16S region.

| Sequence ID | EC 2015a | EC 2011 | MX 2013 | US TX2013c | US TX2006a | HN 2016 | NHP 1996 | US TX2013b | US TX2006b | EC 2015b | US 2013a | NHP MX 2013 |
|---|---|---|---|---|---|---|---|---|---|---|---|---|
| EC2015a | ** | | | | | | | | | | | |
| EC2011 | 100.00 | ** | | | | | | | | | | |
| MX2013 | 99.91 | 99.91 | ** | | | | | | | | | |
| US TX2013c | 99.91 | 99.91 | 100.00 | ** | | | | | | | | |
| US TX2006a | 99.91 | 99.91 | 100.00 | 100.00 | ** | | | | | | | |
| HN 2016 | 99.82 | 99.82 | 99.91 | 99.91 | 99.91 | ** | | | | | | |
| NHP 1996 | 99.82 | 99.82 | 99.91 | 99.91 | 99.91 | 99.82 | ** | | | | | |
| USTX2013b | 99.91 | 99.91 | 100.00 | 100.00 | 100.00 | 99.91 | 99.91 | ** | | | | |
| USTX2006b | 99.91 | 99.91 | 100.00 | 100.00 | 100.00 | 99.91 | 99.91 | 100.00 | ** | | | |
| EC2015b | 100.00 | 100.00 | 99.91 | 99.91 | 99.91 | 99.82 | 99.82 | 99.91 | 99.91 | ** | | |
| US2013a | 99.91 | 99.91 | 100.00 | 100.00 | 100.00 | 99.91 | 99.91 | 100.00 | 100.00 | 99.91 | ** | |
| NHP MX 2013 | 99.64 | 99.64 | 99.73 | 99.73 | 99.73 | 99.64 | 99.82 | 99.73 | 99.73 | 99.64 | 99.73 | ** |

Example 2

Introduction

Acute hepatopancreatic necrosis disease (AHPND, initially referenced to as early mortality syndrome, EMS) is a deadly shrimp disease caused by particular *Vibrio* spp. (J. E. Han et al., 2017; Lee et al., 2015; Tran et al., 2013). This disease first emerged in China in 2009 and has rapidly spread throughout Southeast Asia to Vietnam, Malaysia, Thailand and reached Mexico in Latin America in 2013 (Nunan et al., 2014; Tran et al., 2013). The impact of AHPND in shrimp farming at global scale has been catastrophic with an estimated global loss of $1 billion per year (FAO, 2013).

The pathogenic *Vibrio* spp. harbors a large plasmid that ranges from 69-74 kb, on average of 33 copies per cell, and contains *Photorhabdus* Insect-Related (Pir) toxin genes PirA and PirB (J. E. Han et al., 2017, 2015; Yang et al., 2014). The binary toxin PirAB has been confirmed to be as the etiological agent factor for AHPND (J. Han et al., 2015). To date, two PCR based methods have been reported to detect both toxins genes PirA and PirB, a duplex PCR reported by J. E. Han et al., (2017) and the two-tube nested AP4 PCR developed by Dangtip et al., (2015). For quantification and detection, a qPCR assay that detects PirA has been reported but does not detect type II mutants (J. E. Han et al., 2015). The detection of both types of mutants is fundamental for the study of plasmid transmission dynamics and recording the presence of the virulence plasmid since studies by Lee et al., (2015) that suggest that the PirA and PirB genes may be lost or acquired by horizontal gene transfer via transposition or homologous recombination. In this study we report a SYBR Green real-time PCR that detects the PirA and PirB toxin genes, and two internal control genes the shrimp 18s rRNA and the bacterial 16s rRNA.

Methods

Primer Design

Two primer pairs were designed with Geneious R11 (Kearse et al., 2012) to detect the PirA and PirB toxin genes (Table 3). The primers for the PirB gene were designed to amplify the final section of the PirB gene allowing the detection of *Vibrio* spp. type II mutants (Fig.). The genes used as internal controls for the shrimp and bacteria were the 18S rRNA and 16S rRNA respectively (Table 4).

TABLE 3

Primers for the detection of PirA and PirB toxin genes. For each primer the sequence, the Tm, product size and the location on the virulence plasmid from reference strain A3 (GenBank accession: KM067908.1) is shown.

| Primer Set | Primer pair | Primer sequence (5' to 3') | Primer Tm | Product size (bp) | Location of reference strain A3 |
|---|---|---|---|---|---|
| Set 1 | PirA F1 | TGAAACTGACTATTCTCACGATTG (SEQ ID NO: 8) | 57 | 80 | 17,218 → 17,241 |
| | PirA R1 | TGATAGGTGTATGTTTGCTGTC (SEQ ID NO: 9) | 56.2 | 80 | 17,297 → 17,276 |
| | PirB F1 | TCACGGCTTTGAACATATGC (SEQ ID NO: 10) | 56.8 | 149 | 18,268 → 18,287 |
| | PirB R1 | CATCTTCCGTACCTGTAGCA (SEQ ID NO: 11) | 56.8 | 149 | 18,416 → 18,397 |

TABLE 4

Internal control primers. For each primer, the sequence, the Tm, product size and the reference is shown. The genes used as internal controls were the shrimp 18S rRNA and the bacterial 16S rRNA.

| Gene | Primer pair | Primer sequence (5' to 3') | Primer Tm | Product size (bp) | Reference |
|---|---|---|---|---|---|
| 16S rRNA | 16S-rRNAF | TCCTACGGGAGGCAGCAGT (SEQ ID NO: 12) | 59.4 | 466 | (Nadkarni et al., 2002) |
| | 16S-rRNAR | GGACTACCAGGGTATCTAATCCTGTT (SEQ ID NO: 13) | 58.1 | | |
| 18S rRNA Set 1 | 18S rRNA F1 | GAGAGGGAGCCTGAGAAACG (SEQ ID NO: 14) | 59.8 | 72 | This example |
| | 18S rRNA r1 | GTGCCGGGAGTGGGTAATTT (SEQ ID NO: 15) | 60.3 | | |

Multiplex Real-Time SYBR Green PCR.

Multiplex real-time SYBER Green PCR was performed using a StepOnePlus Real-Time PCR System (Appliedbiosystems™). Each assay was carried out in a total volume of 20 μl containing 1 μl of template DNA, 10 μl of PowerUp™ SYBR™ Green Master Mix (2×), 150 nM of PirA, 450 nM of PirB primers, 200 nM of 18S rRNA shrimp internal control primers, 300 nM of 16S rRNA bacteria internal control. The real-time PCR conditions consisted of a UDG activation at 50° C. for 2 min, denature and Dual-Lock™ DNA polymerase activation at 95° C. for 2 min, followed by 40 cycles at 95° C. for 3 s and 59° C. for 30 s. Following amplification, the melt curve analysis was performed. The reaction temperature was increased to 95° C. for 15 s, then decreased to 60° C. for 1 min, and increased to 95° C. at a rate 0.15° C. per s, with continuous fluorescence monitoring. The melt curves were used to determine if the primers were compatible, only primer combinations that showed 4 clear specific amplification peaks were considered adequate for the multiplex real-time PCR.

Bacteria

Three natural known mutant strains of *V. parahaemolyticus*, three strains of AHPND causing *V. campbelli* and ten strains of AHPND causing *V. Parahaemolyticus* were obtained from the Aquaculture pathology laboratory bacterial collection, these bacteria were originally isolated from either stomachs of diseased shrimp, water or sediments from AHPND-affected farms in Asia or Latin America during 2013-2018. The bacteria were used to test the PirA, PirB and internal control primers (18S rRNA and 16S rRNA). Additionally, the HP of 10 AHPND infected shrimp were tested with the mentioned primers.

Positive Control for qPCR

The DNA fragments for the PirA (80 bp), PirB (149 bp) were amplified from *V. parahaemolyticus* 18-408 and cloned into pDrive Cloning Vector (QIAGEN®). The plasmids were designated VpPirA80 and VpPirB149. The plasmids were purified using QIAprep® Spin Miniprep Kit. The sequence of the PirA and PirB fragments was verified by sequencing at the sequencing facility of The University of Arizona.

Sensitivity

The sensitivity of the qPCR assay was determined using 6-fold serial dilutions of purified VpPirA80 plasmid and a 5-fold serial dilution of VpPirB149 plasmid. The concentrations of plasmid DNA that were utilized ranged from $10^2$ to $10^6$ copies/μl for VpPirA80 and from $10^1$ to $10^5$ copies/μl for VpPirB149.

Results

Multiplex Real-Time SYBR Green PCR.

Figure 9:
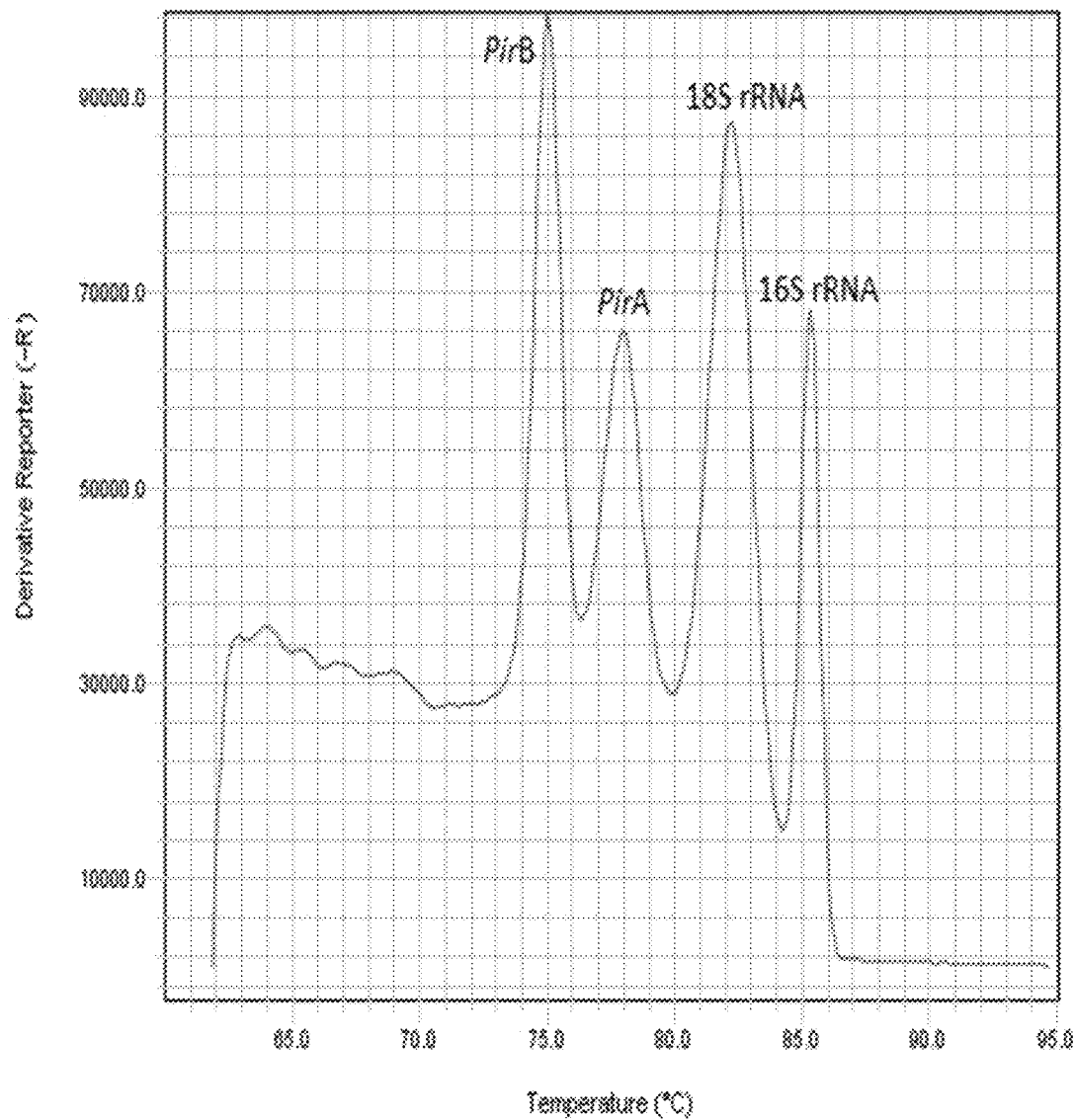
FIG. 9 shows a graph that demonstrates results from a melt curve analysis of PirA, PirB, 18S rRNA and 16S rRNA their melting temperatures are 78.24±0.16, 75.20±0.17, 82.57±0.28 and 85.39±0.18° C. respectively. Each amplicon shows a clearly defined peak.

The amplicons for PirA, PirB, 18S rRNA and 16S rRNA from infected AHPND infected shrimp all showed easily distinguishable melting temperatures of 78.24±0.16, 75.20±0.17, 82.57±0.28 and 85.39±0.18° C. respectively (FIG. 9).

Bacteria

Figure 10:
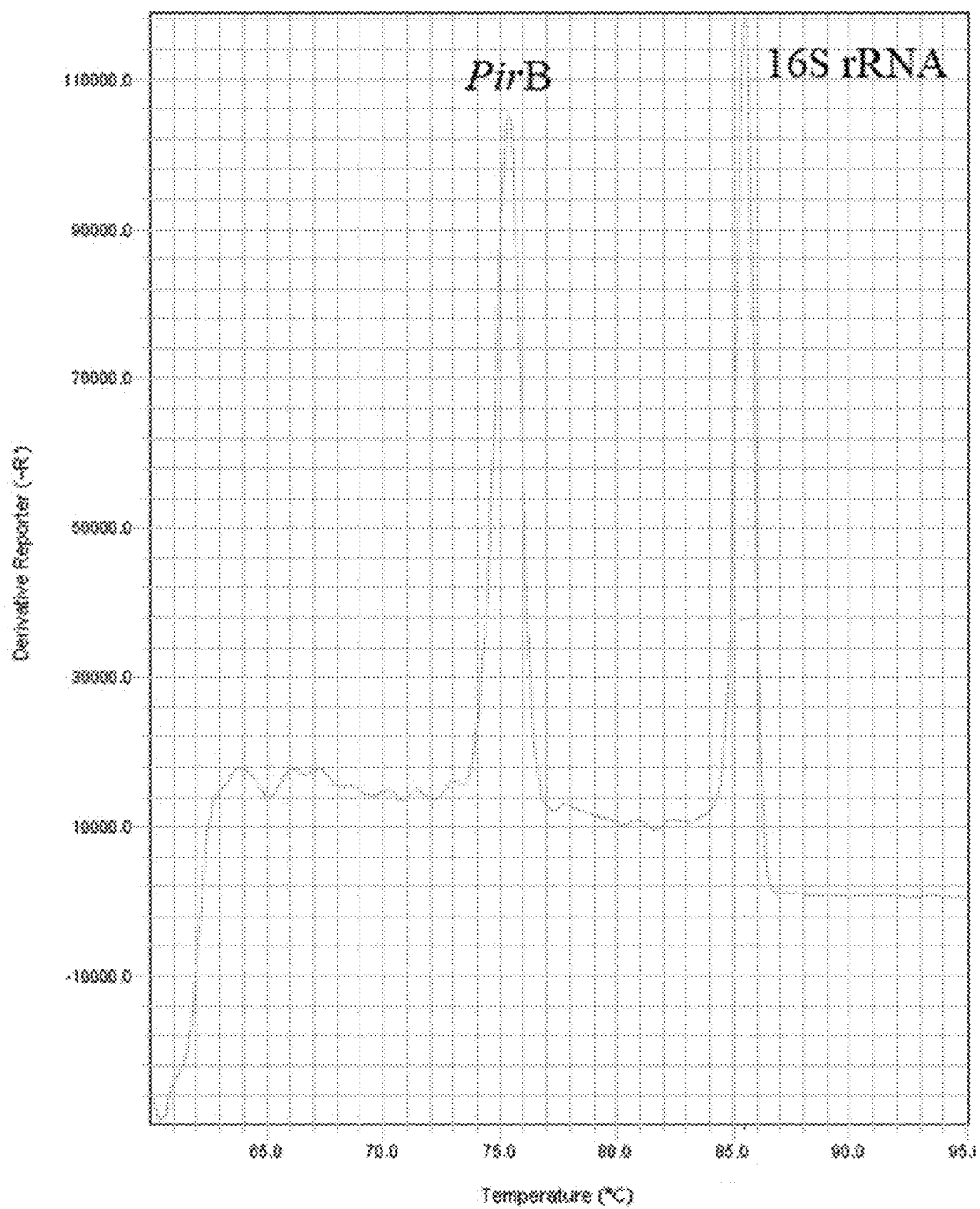
FIG. 10 shows a graph that demonstrates results from a melt curve analysis of V. parahaemolyticus PirA negative strain. The melting temperatures of PirB and 16S rRNA are 75.20±0.17 and 85.39±0.18° C. respectively. Each amplicon shows a clearly defined peak.
Figure 11:
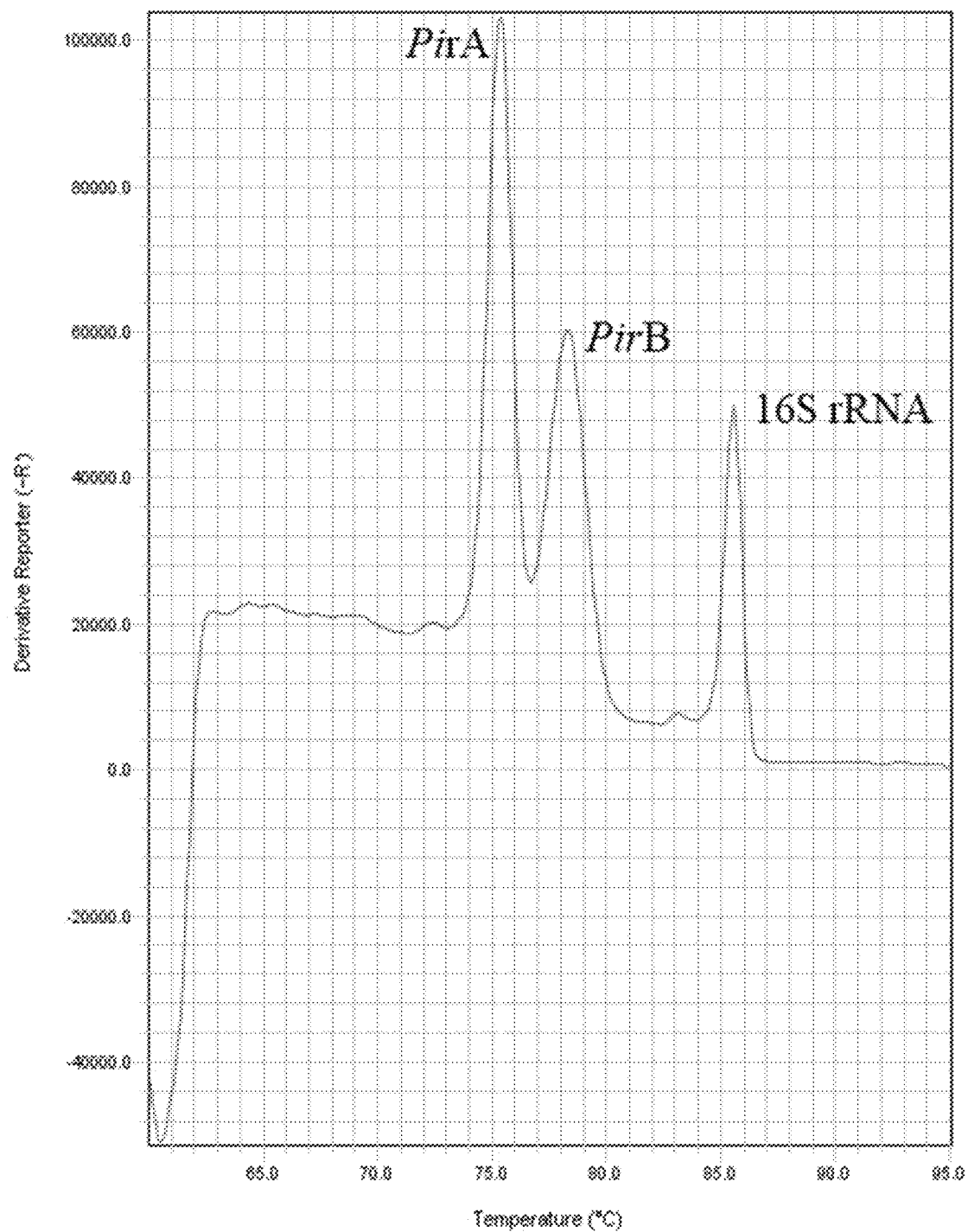
FIG. 11 shows a graph that demonstrates results from a melt curve analysis AHPND causing strains of Vibrio spp. The melting temperatures of PirA, PirB and 16S rRNA are 78.24±0.16, 75.20±0.17 and 85.39±0.18° C. respectively. Each amplicon shows a clearly defined peak.

The real-time PCR results for the different strains of bacteria are shown in table 4. The PirA negative *V. parahaemolyticus* strains showed two amplicons, PirB and 16S rRNA, with melting temperatures of 75.20±0.16 and 85.39±0.18° C. respectively (FIG. 10). The AHPND causing strains showed three amplicons, PirA, PirB and 16S rRNA, with melting temperatures of 78.24±0.16, 75.20±0.17 and 85.39±0.18° C. respectively (FIG. 11).

TABLE 5

| Strain | Notes | PirA | PirB | 18S rRNA | 16S rRNA |
|---|---|---|---|---|---|
| DA 16-250-8 | *V. parahaemolyticus* PirA negative | Neg | Pos | Neg | Pos |
| D 16-250-9 | *V. parahaemolyticus* PirA negative | Neg | Pos | Neg | Pos |
| DB 16-250 | *V. parahaemolyticus* PirA negative | Neg | Pos | Neg | Pos |
| D 16-192 | *V. campbelli* AHPND | Pos | Pos | Neg | Pos |
| D3 16-137 | *V. campbelli* AHPND | Pos | Pos | Neg | Pos |
| D 52 B | *V. campbelli* AHPND | Pos | Pos | Neg | Pos |
| 13-028 A3 | Reference strain | Pos | Pos | Neg | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |

TABLE 5-continued

| Strain | Notes | PirA | PirB | 18S rRNA | 16S rRNA |
| --- | --- | --- | --- | --- | --- |
| Infected tissue | Challenge test (Jun. 19, 2018) | Pos | Pos | Pos | Pos |
| Infected tissue | Challenge test (Jun. 19, 2018) | Pos | Pos | Pos | Pos |
| Infected tissue | Challenge test (Jun. 19, 2018) | Pos | Pos | Pos | Pos |

Sensitivity

Figure 12A:
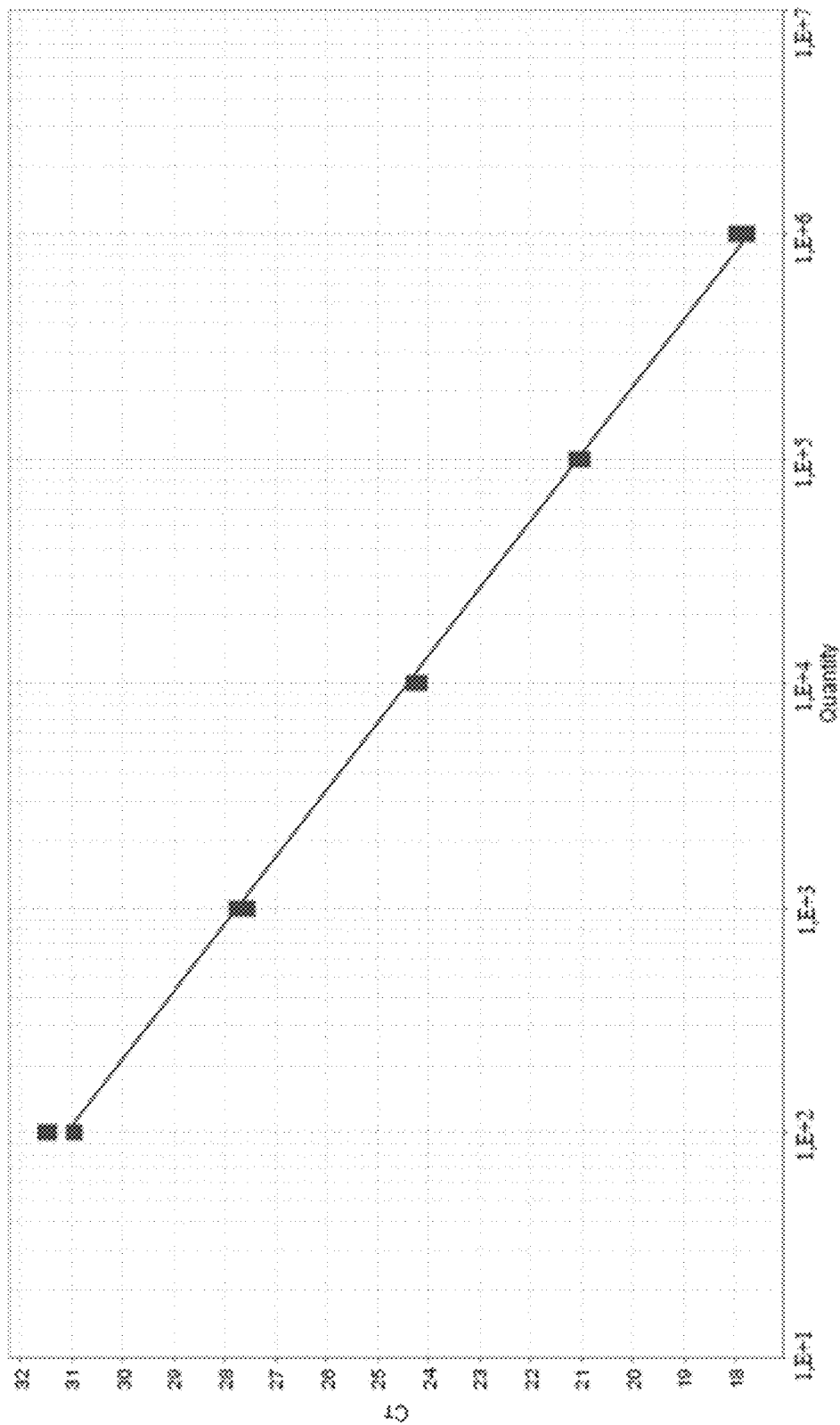
FIGS. 12A-12B shows a graph demonstrating the Standard curves for PirA and PirB.
Figure 12B:
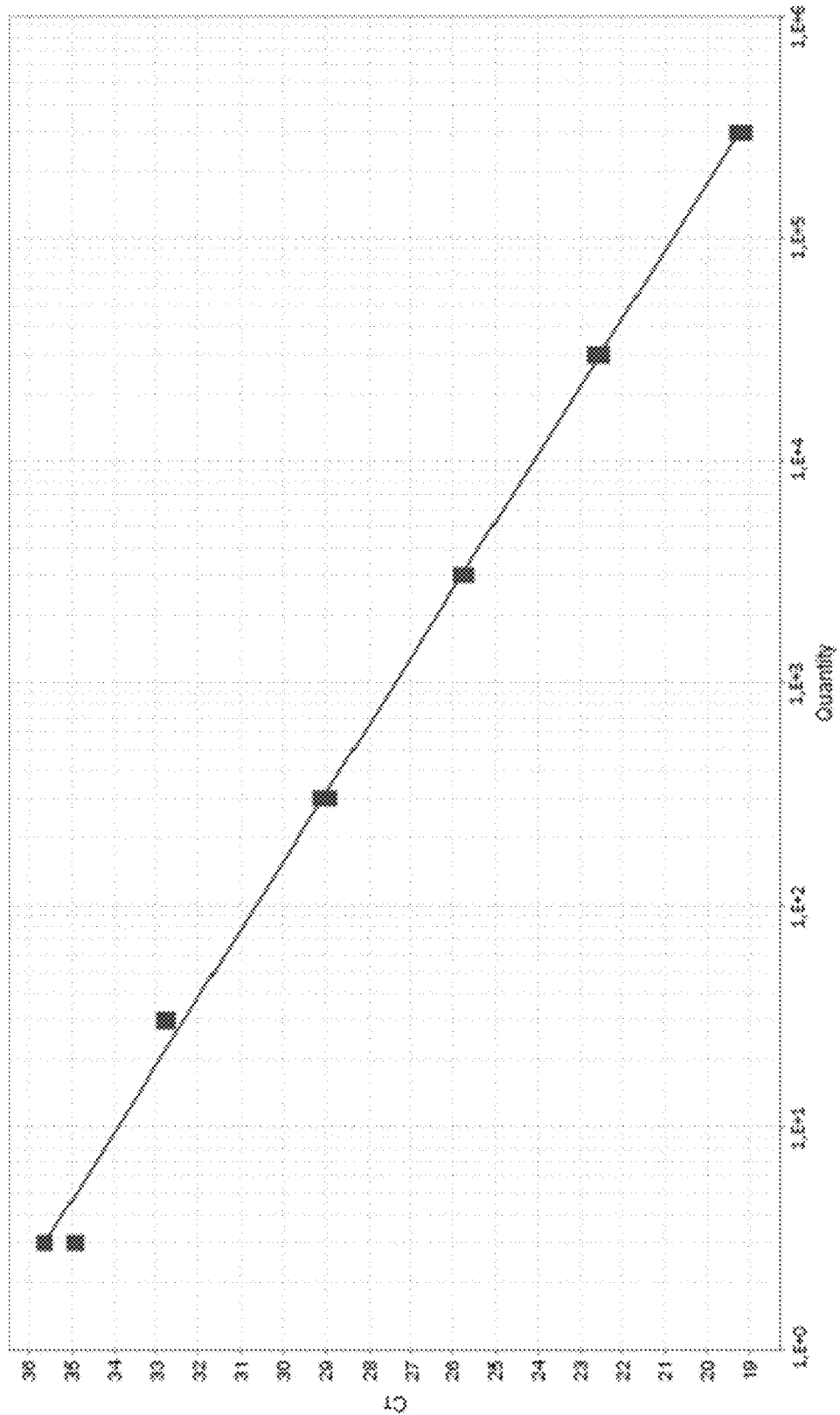

The lower limit of detection of the PirA and PirB primers were 100 copies and 10 copies respectively of recombinant plasmid containing these genes (FIGS. 12A-12B).

REFERENCES

Dangtip, S., Sirikharin, R., Sanguanrut, P., Thitamadee, S., Sritunyalucksana, K., Taengchaiyaphum, S., Mavichak, R., Proespraiwong, P., Flegel, T. W., 2015. AP4 method for two-tube nested PCR detection of AHPND isolates of *Vibrio parahaemolyticus*. Aquac. Reports 2, 158-162. doi:10.1016/j.aqrep.2015.10.002

Dhar, A. K., Bowers, R. M., Licon, K. S., Veazey, G., Read, B., 2009. Validation of reference genes for quantitative measurement of immune gene expression in shrimp. Mol. Immunol. 46, 1688-1695. doi:10.1016/j.molimm.2009.02.020

FAO, 2013. Report of the FAO/MARD Technical Workshop on Early Mortality Syndrome (EMS) or Acute Hepatopancreatic Necrosis Syndrome (AHPNS) of Cultured Shrimp (under TCP/VIE/3304) [WWW Document]. FAO Fish. Aquac. Rep. URL http://www.fao.org/docrep/018/i3422e/i3422e.pdf Han, J., Tang, K., Tran, L., Lightner, D., 2015. *Photorhabdus* insect-related (Pir) toxin-like genes in a plasmid of *Vibrio parahaemolyticus*, the causative agent of acute hepatopancreatic necrosis disease (AHPND) of shrimp. Dis. Aquat. Organ. 113, 33-40. doi:10.3354/dao02830

Han, J. E., Tang, K. F. J., Aranguren, L. F., Piamsomboon, P., 2017. Characterization and pathogenicity of acute hepatopancreatic necrosis disease natural mutants, pir AB vp (−) *V. parahaemolyticus*, and pir AB vp (+) *V. campbellii* strains. Aquaculture 470, 84-90. doi:10.1016/j.aquaculture.2016.12.022

Han, J. E., Tang, K. F. J., Aranguren, L. F., Piamsomboon, P., 2017. Characterization and pathogenicity of acute hepatopancreatic necrosis disease natural mutants, pirA-Bvp(−) *V. parahaemolyticus*, and pirABvp(+) *V. campbellii* strains. Aquaculture 470, 84-90. doi:10.1016/j.aquaculture.2016.12.022

Han, J. E., Tang, K. F. J., Pantoja, C. R., White, B. L., Lightner, D. V., 2015. QPCR assay for detecting and quantifying a virulence plasmid in acute hepatopancreatic necrosis disease (AHPND) due to pathogenic *Vibrio parahaemolyticus*. Aquaculture 442, 12-15. doi: 10.1016/j.aquaculture.2015.02.024

Kearse, M., Moir, R., Wilson, A., Stones-Havas, S., Cheung, M., Sturrock, S., Buxton, S., Cooper, A., Markowitz, S., Duran, C., Thierer, T., Ashton, B., Meintjes, P., Drummond, A., 2012. Geneious Basic: An integrated and extendable desktop software platform for the organization and analysis of sequence data. Bioinformatics 28, 1647-1649. doi:10.1093/bioinformatics/bts199

Lee, C.-T., Chen, I.-T., Yang, Y.-T., Ko, T.-P., Huang, Y.-T., Huang, J.-Y., Huang, M.-F., Lin, S.-J., Chen, C.-Y., Lin, S.-S., Lightner, D. V., Wang, H.-C., Wang, A. H.-J., Wang, H.-C., Hor, L.-I., Lo, C.-F., 2015. The opportunistic marine pathogen *Vibrio parahaemolyticus* becomes virulent by acquiring a plasmid that expresses a deadly toxin. Proc. Natl. Acad. Sci. 112, 10798-10803. doi:10.1073/pnas.1503129112

Nadkarni, M., Martin, F. E., Jacques, N. A., Hunter, N., 2002. Determination of bacterial load by real-time PCR using a broad range (universal) probe and primer set. Microbiology 148, 257-266. doi:10.1128/JCM.40.5.1698

Nunan, L., Lightner, D., Pantoja, C., Gomez-jimenez, S., 2014. Detection of acute hepatopancreatic necrosis disease (AHPND) in Mexico 111, 81-86. doi:10.3354/dao02776

Tran, L., Nunan, L., Redman, R., Mohney, L., Pantoja, C., Fitzsimmons, K., Lightner, D., 2013. Determination of the infectious nature of the agent of acute hepatopancreatic necrosis syndrome affecting penaeid shrimp. Dis. Aquat. Organ. 105, 45-55. doi:10.3354/dao02621

Yang, Y., Chen, I., Lee, C., Chen, C., Lin, S., Hor, L., Tseng, T., Huang, Y., 2014. Draft Genome Sequences of Four Strains of *Vibrio parahaemolyticus*, Three of Which Cause Early Mortality Syndrome/Acute. Genome 2, 2-3. doi:10.1128/genomeA.00816-14.

SEQUENCE LISTING

SEQ ID NO: 1 (primer for detecting H. penaei (NHP FlgE 1143F))
5'-AGG-CAA-ACA-AAC-AAC-CCT-TG-3'

SEQ ID NO: 2 (primer for detecting H. penaei (NHP flgE1475R))
5'-GCG-TTG-TTG-TTG-GGA-AAG-TT-3'

SEQ ID NO: 3 (primer for TaqMan probe fore flgE of H. penaei) (NHP FlgE3qF)
5'-AAC-ACC-CTG-TCT-CCC-CAA-TTC-3'

SEQ ID NO: 4 (primer for TaqMan probe fore flgE of H. penaei) (NHP FlgE3qR)
5'-CCA-GCC-TTG-GAC-AAA-CAC-CTT-3')

SEQ ID NO: 5 (TaqMan probe for flgE of H. penaei)
5'-CGC-CCC-AAA-GCA-TGC-CGC-3'

SEQ ID NO: 6 (Oligonucleotide primer NHP16S rRNA F2)
5'-GTG-GCA-GAC-GGG-TGA-GTA-AT-3'

SEQ ID NO: 7 (oligonucleotide primer NHP16S rRNAR2)
5'-CCT-CCA-TTG-CTG-GTT-AGC-TC-3',

SEQUENCE LISTING

SEQ ID NO: 8 (primer PirA F1)
TGAAACTGACTATTCTCACGATTG

SEQ ID NO: 9 (primer PirA R1)
TGATAGGTGTATGTTTGCTGTC

SEQ ID NO: 10 (primer PirB F1)
TCACGGCTTTGAACATATGC

SEQ ID NO: 11 (primer PirB R1)
CATCTTCCGTACCTGTAGCA

SEQ ID NO: 12 (primer 16S-rRNAF)
TCCTACGGGAGGCAGCAGT

SEQ ID NO: 13 (primer 16S-rRNAR)
GGACTACCAGGGTATCTAATCCTGTT

SEQ ID NO: 14 (primer 18S rRNA F1)
GAGAGGGAGCCTGAGAAACG

SEQ ID NO: 15 (primer 18S rRNA r1)
GTGCCGGGAGTGGGTAATTT

SEQ ID NO: 16 (flgE of *H. penaei* (GenBank JQAJ01000001.1)
ATGCCAACATCACCTAACGAGATTGTTCGCGCTGTCCCCGCCTTTTGCACC
CAAGGCGATGCCTCAGATATCTCTGCCACAGGCATGGATGTATATGAAGAAGGTGT
GGCTCATTTTGCTAAGCATTTGGCGAATGTGAAACCATAGGCTATATGCACGACA
ACCTGTGCCATCTGACCAATGGTCCCCATGGTGAAACCGTGCGCGGCGTGGAGAT
GAACAATTTTGACGTGAGTGCCAGAGGTCCGATGCGCCATACCGAGCGCGAGCTG
GACATCGGTGTGCGGGGGCGTGGGTTTTTGTTGGTGGATGCGTCAGGCAGCGCA
GATGAAAGCGCCGACACCCTTCCGTGCGCTAAAACCACCGGTAGTTTTCAGGTGG
ATGCCAGCGGCTATGTCTATGATGAAGGCGGCAACACCTTGTTGGGCAAAAAAATT
AACAACGATGGCACCGTGGATCCCTGCAGCCTCATGTCTGATCTCGATCGCGTAAA
AATGCCCATGACCTTTAACCAGGCCGATGCCACCGAAAATGTCAGATTCAACGGCA
TTTTACCTGCTGATAACGTGTCTCTTGGTGACACCCATGAAAGCGCCGTGGATGTG
GCGGATTCACTCGGGGTAGGTCACCAGTTTCGCTTTACCTGGACCTTTTTGGCCCC
ACGCGTGTGGCAAATGACCCTTCAAGATTCCACCAACACACCGGTGTTTCAAGAGA
CAGCTGGTGGTAACTCATGGGTCGATGGCAACAATGCTGATGGCATTTTGCCACG
CGCGGTGGCGCCGTGGTTCATTTTACAGAAAATGGGGATTATAGTGGCGCCGTGG
CGGCCACAGACGCCAATTATGTGGCGTGGGATAATGCCTTGCGTGCCTATGAAGC
GGCGAAGATCGTGAACGACCACGCCACCATCTTGTTAGACACCAACCCCACCATGA
CCAAAGCCGATTTTGACGCTCAAATTATGGCCTTTGCGCTTGCCACTTATCCTGCCA
GAAATCTGGCTGCTGCAGATACCATTGAATATACATCGTCTCAAGACATTGTTGCGG
ACCTGACCGGTGTTGCAGGCACTATTGGTGTTGGCGGGCCCTTTGTGAACGTCAAT
GCCATCAAAGCAGCGGGCACCACAGACATCACAGGCAAACAAACAACCCTTGGTA
*ACACGTGGAACACCCTGTCTCCCCAATTCACGCCCCAAAGCATGCCGCCTAAGGT*
*GTTTGTCCAAGGCTGGCTCAACAGCGAAGGGGTGCCTGTGGGATCAGCAGACAGC*
*ACCATTGCCCTAGATCCCAGCACCATGGCTCTTTCTGGCAACCAATATCAACTGCA*
*AACGCCCGAGCAAGATGGGCGTATGGCCGCCCCTTTCAAAGGCATTAGCATCAGC*
*GATACCGGGGTGATTTCTTCTGAATTTTTTGGTCAAGACCCCAAACCTGAATGGCA*
*GTTGTTTTTGGT*AACTTTCCCAACAACAACGCCATGGAGCAACATGGGAGGAAC
CTGCTTCTTCCCACCATTGAGTGTGGCGACCCTTATGTGCTTTCTACCCCACTTACC
TCCAATTTGGGGGCCACACAGGCCAAATCTCTGGTGACATCCAACGTAGATGATAC
AAAAACCATGTTAGGGAGCCAAAAAATGTCGATGGCCACGCAAATGAACACCACGG
TGTTCAAAATCGCGGTGGATCTTGACAAGTTCATTATTGGCATGATCTCACAAACGG
CCTAA Bold: Binding sequences for the FlgE forward and reverse primers (SEQ ID NOs.: 1 and 2, resepctively).
Underlined region: ~333 bp flgE amplicon.
Italicized and Underlined region: Binding sights for Forward and Reverse primers (SEQ ID NOs.: 3 and 4)
Double underlined region: Binding site for Taqman Probe.

What is claimed is:

1. An assay comprising:
amplifying a fragment of the flgE gene of *Hepatobacter penaei* (*H. penaei*) using a polymerase chain reaction (PCR) method, wherein the step of amplifying comprises
contacting a nucleic acid sample obtained from one or more shrimp with a first oligonucleotide primer and a second oligonucleotide primer,
wherein the first oligonucleotide primer is a forward direction oligonucleotide primer adapted for PCR amplification of a fragment of the flgE gene of *H. penaei* with the second oligonucleotide primer and specifically binds a region of the flgE gene of *H. penaei*,
wherein the second oligonucleotide primer is a reverse direction oligonucleotide primer adapted for PCR amplification of a fragment of the flgE gene of *H. penaei* with the first oligonucleotide primer and specifically binds a region of the flgE gene of *H. penaei*; and
detecting the presence or absence of an amplified double stranded DNA fragment of the flgE gene in the nucleic acid sample.

2. The assay of claim 1, wherein the step of amplifying further comprises contacting the nucleic acid sample with a first oligonucleotide probe adapted for real-time PCR amplification and detection, wherein the first oligonucleotide probe specifically binds a region of the flgE gene that is between the region of the flgE gene where the first oligonucleotide primer specifically binds and the region of the flgE gene where the second oligonucleotide primer specifically binds, and wherein the first oligonucleotide probe is coupled to a fluorophore and a quencher molecule.

3. The assay of claim 2, wherein the fluorophore of the first oligonucleotide probe is released during the step of amplifying and produces detectable fluorescence.

4. The assay of claim 1, wherein the step of amplifying further comprises contacting the amplified double stranded DNA fragment of the flgE gene with a detectable dye molecule that binds double stranded DNA.

5. The assay of claim 2, wherein the step of amplifying further comprises contacting the nucleic acid sample with a third oligonucleotide primer and a fourth oligonucleotide primer,
wherein the third oligonucleotide primer is a forward direction oligonucleotide primer adapted for PCR amplification of a fragment of the beta actin gene or the 18S rRNA gene of shrimp with the fourth oligonucleotide primer and specifically binds a region of the beta actin gene or the 18S rRNA gene of shrimp,
wherein the fourth oligonucleotide primer is a reverse direction oligonucleotide primer adapted for PCR amplification of a fragment of the beta actin gene or the 18S rRNA gene of shrimp with the third oligonucleotide primer and specifically binds a region of the beta actin gene or the 18S rRNA gene of shrimp, and
wherein the step of detecting further includes detecting the presence or absence of an amplified double stranded DNA fragment of the beta actin gene or the 18S rRNA gene of shrimp in the nucleic acid sample.

6. The assay of claim 5, wherein the step of amplifying the flgE gene fragment and the step of amplifying the beta actin gene or the 18S rRNA gene of shrimp is carried out in the same PCR reaction.

7. The assay of claim 5, wherein the step of amplifying further comprises contacting the nucleic acid sample with a second oligonucleotide probe adapted for real-time PCR amplification and detection, wherein the second oligonucleotide probe specifically binds a region of the beta actin gene or the 18S rRNA gene of shrimp that is between the region of the beta actin gene or the 18S rRNA gene of shrimp where the third oligonucleotide primer specifically binds and the region of the beta actin gene or 18S rRNA gene of shrimp gene where the fourth oligonucleotide primer specifically binds, and wherein the second oligonucleotide probe is coupled to a fluorophore and a quencher molecule.

8. The assay of claim 7, wherein the fluorophore of the second oligonucleotide probe is released during the step of amplifying and produces detectable fluorescence.

9. The assay of claim 5, wherein the step of amplifying further comprises contacting the amplified double stranded DNA fragment of the beta actin gene or the 18S rRNA gene of shrimp with a detectable dye molecule that binds double stranded DNA.

10. The assay of claim 9, wherein the step of contacting the amplified double stranded DNA fragment of the beta actin gene or the 18S rRNA gene of shrimp with a detectable dye molecule that binds double stranded DNA occurs during the step of amplifying.

11. The assay of claim 5, wherein the first oligonucleotide primer has a sequence according to SEQ ID NO: 1 or 3; the second oligonucleotide primer has a sequence according to SEQ ID NO: 2 or 4; or any combination thereof; the first oligonucleotide probe comprises a sequence according to SEQ ID NO: 5; the third primer has a sequence according to SEQ ID NO: 14; the fourth primer has a sequence according to SEQ ID NO.: 15; or any combination thereof.

12. The assay of claim 5, wherein the step of amplifying further comprises contacting the nucleic acid sample with a fifth oligonucleotide primer and a sixth oligonucleotide primer and/or a seventh oligonucleotide primer and an eighth oligonucleotide primer,
wherein the fifth oligonucleotide primer is a forward direction oligonucleotide primer adapted for PCR amplification of a fragment of the pirA gene of *V. parahaemolyticus* with the sixth oligonucleotide primer and specifically binds a region of the pirA gene of *V. parahaemolyticus*,
wherein the sixth oligonucleotide primer is a reverse direction oligonucleotide primer adapted for PCR amplification of a fragment of the pirA gene of *V. parahaemolyticus* with the fifth oligonucleotide primer and specifically binds a region of the pirA gene of *V. parahaemolyticus*,
wherein the seventh oligonucleotide primer is a forward direction oligonucleotide primer adapted for PCR amplification of a fragment of the pirB gene of *V.*

*parahaemolyticus* with the eighth oligonucleotide primer and specifically binds a region of the pirB gene of *V. parahaemolyticus*, wherein the eighth oligonucleotide primer is a reverse direction oligonucleotide primer adapted for PCR amplification of a fragment of the pirB gene of *V. parahaemolyticus* with the seventh oligonucleotide primer and specifically binds a region of the pirB gene of *V. parahaemolyticus*, and wherein the step of detecting further includes detecting the presence or absence of an amplified double stranded DNA fragment of the pirA gene and/or the pirB gene of *V. parahaemolyticus* in the nucleic acid sample.

13. The assay of claim 12, wherein the step of amplifying further comprises contacting the nucleic acid sample with a ninth oligonucleotide primer and a tenth oligonucleotide primer, wherein the ninth oligonucleotide primer is a forward direction oligonucleotide primer adapted for PCR amplification of a fragment of the 16S rRNA gene of *V. parahaemolyticus* with the tenth oligonucleotide primer and specifically binds a region of the 16S rRNA gene of *V. parahaemolyticus*, wherein the tenth oligonucleotide primer is a reverse direction oligonucleotide primer adapted for PCR amplification of a fragment of the 16S rRNA gene of *V. parahaemolyticus* with the ninth oligonucleotide primer and specifically binds a region of the 16S rRNA gene of *V. parahaemolyticus*, and wherein the step of detecting further includes detecting the presence or absence of an amplified double stranded DNA fragment of the 16S rRNA gene of *V. parahaemolyticus* in the nucleic acid sample.

14. The assay of claim 13, wherein the step of amplifying further comprises contacting the nucleic acid sample with a third oligonucleotide probe and/or a fourth oligonucleotide probe adapted for real-time PCR amplification and detection, wherein the third oligonucleotide probe specifically binds a region of the pirA gene that is between the region of the pirA gene where the fifth oligonucleotide primer specifically binds and the region of the pirA gene where the sixth oligonucleotide primer specifically binds, wherein the fourth oligonucleotide probe specifically binds a region of the pirB gene that is between the region of the pirB gene where the seventh oligonucleotide primer specifically binds and the region of the pirB gene where the eighth oligonucleotide primer specifically binds, and wherein the third and the fourth oligonucleotide probes are each coupled to a fluorophore and a quencher molecule.

15. The assay of claim 14, wherein the fluorophore of the third oligonucleotide probe and/or the fourth oligonucleotide probe is/are released during the step of amplifying and produce(s) detectable fluorescence.

16. The assay of any one of claim 15, wherein the fifth oligonucleotide primer has a sequence according to SEQ ID NO: 8; the sixth oligonucleotide primer has a sequence according to SEQ ID NO: 9; the seventh oligonucleotide primer has a sequence according to SEQ ID NO: 10; the eighth oligonucleotide primer has a sequence according to SEQ ID NO: 11; the ninth oligonucleotide primer has a sequence according to SEQ ID NO: 12; the tenth oligonucleotide primer has a sequence according to SEQ ID NO: 13; or any combination thereof.

17. The assay of claim 14, wherein the step of amplifying further comprises contacting the nucleic acid sample with a fifth oligonucleotide probe adapted for real-time PCR amplification and detection, wherein the fifth oligonucleotide probe specifically binds a region of the 16S rRNA gene of *V. parahaemolyticus* that is between the region of the 16S rRNA gene of *V. parahaemolyticus* where the ninth oligonucleotide primer specifically binds and the region of the 16S rRNA gene of *V. parahaemolyticus* where the tenth oligonucleotide primer specifically binds, and wherein the fifth oligonucleotide probe is coupled to a fluorophore and a quencher molecule.

18. The assay of claim 17, wherein the fluorophore of the fifth oligonucleotide probe is released during the step of amplifying and produces detectable fluorescence.

19. The assay of claim 17, wherein the step of amplifying further comprises contacting the amplified double stranded DNA fragment of the pirA gene, the pirB gene, the 16s rRNA gene of *V. parahaemolyticus*, the beta actin gene of shrimp, the 18S rRNA gene of shrimp, or any combination thereof with a detectable dye molecule that binds double stranded DNA.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:

<223> OTHER INFORMATION: Synthetic Construct

<400> SEQUENCE: 1
aggcaaacaa acaacccttg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gcgttgttgt tgggaaagtt                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
aacaccctgt ctccccaatt c                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ccagccttgg acaaacacct t                                             21

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
cgccccaaag catgccgc                                                 18

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gtggcagacg ggtgagtaat                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cctccattgc tggttagctc                                               20

```
<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
tgaaactgac tattctcacg attg                                          24

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
tgataggtgt atgtttgctg tc                                            22

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tcacggcttt gaacatatgc                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
catcttccgt acctgtagca                                               20

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
tcctacggga ggcagcagt                                                19

<210> SEQ ID NO 13
<211> LENGTH: 26
<212> TYPE: DNA
<213> ORGANISM: Artificial Sequence
<220> FEATURE:
<223> OTHER INFORMATION: Synthetic Construct

<400> SEQUENCE: 13
ggactaccag ggtatctaat cctgtt                                        26

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 14
gagagggagc ctgagaaacg                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gtgccgggag tgggtaattt                                          20

<210> SEQ ID NO 16
<211> LENGTH: 1728
<212> TYPE: DNA
<213> ORGANISM: Hepatobacter penaei

<400> SEQUENCE: 16

```
atgccaacat cacctaacga gattgttcgc gctgtccccg ccttttgcac ccaaggcgat     60
gcctcagata tctctgccac aggcatggat gtatatgaag aaggtgtggc tcattttgct    120
aagcatttgg cgaatgtgga aaccataggc tatatgcacg caacctgtg ccatctgacc     180 aatggtcccc atggtgaaac cgtgcgcggc gtggagatga caattttga cgtgagtgcc     240 agaggtccga tgcgccatac cgagcgcgag ctggacatcg tgtgcgggg cgtgggttt     300 tgttggtgg atgcgtcagg cagcgcagat gaaagcgccg acacccttcc gtgcgctaaa    360
accaccggta gttttcaggt ggatgccagc ggctatgtct atgatgaagg cggcaacacc    420
ttgttgggca aaaaaattaa caacgatggc accgtggatc cctgcagcct catgtctgat    480
ctcgatcgcg taaaaatgcc catgaccttt aaccaggccg atgccaccga aaatgtcaga    540
ttcaacggca tttacctgc tgataacgtg tctcttggtg acacccatga aagcgccgtg    600
gatgtggcgg attcactcgg ggtaggtcac cagtttcgct ttacctggac cttttggcc    660 ccacgcgtgt ggcaaatgac ccttcaagat tccaccaaca caccggtgtt tcaagagaca    720
gctggtggta actcatgggt cgatggcaac aatgctgatg cattttttgc cacgcgcggt    780
ggcgccgtgg ttcattttac agaaaatggg gattatagtg gcgccgtggc ggccacagac    840
gccaattatg tggcgtggga taatgccttg cgtgcctatg aagcggcgaa gatcgtgaac    900
gaccacgcca ccatcttgtt agacaccaac cccaccatga ccaaagccga ttttgacgct    960
caaattatgg cctttgcgct tgccacttat cctgccagaa atctggctgc tgcagatacc   1020
attgaatata catcgtctca agacattgtt gcggacctga ccggtgttgc aggcactatt   1080
ggtgttggcg ggccctttgt gaacgtcaat gccatcaaag cagcgggcac cacagacatc   1140
acaggcaaac aaacaaccct tggtaacacg tggaacaccc tgtctcccca attcacgccc   1200
caaagcatgc cgcctaaggt gtttgtccaa ggctggctca cagcgaagg ggtgcctgtg   1260 ggatcagcag acagcaccat tgccctagat cccagcacca tggctctttc tggcaaccaa   1320
tatcaactgc aaacgcccga gcaagatggg cgtatggccg cccctttcaa aggcattagc   1380
atcagcgata ccggggtgat tcttctgaa ttttttggtc aagaccccaa acctgaatgg   1440
cagttgtttt tggtgaactt tcccaacaac aacgccatgg agcaacatgg gaggaacctg   1500
cttcttccca ccattgagtg tggcgaccct tatgtgcttt ctaccccact tacctccaat   1560
ttgggggcca cacaggccaa atctctggtg acatccaacg tagatgatac aaaaaccatg   1620
```

-continued

```
ttagggagcc aaaaaatgtc gatggccacg caaatgaaca ccacggtgtt caaaatcgcg   1680
gtggatcttg acaagttcat tattggcatg atctcacaaa cggcctaa              1728
```